(12) United States Patent
Callewaert et al.

(10) Patent No.: US 11,964,002 B2
(45) Date of Patent: Apr. 23, 2024

(54) MEANS AND METHODS FOR ORAL PROTEIN DELIVERY

(71) Applicants: VIB VZW, Ghent (BE); UNIVERSITEIT GENT, Ghent (BE)

(72) Inventors: Nico Callewaert, Nevele (BE); Robin Vanluchene, Tielt (BE); Bram Laukens, Ghent (BE); Anna Depicker, Schelderode (BE); Vikram Virdi, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 16/489,265

(22) PCT Filed: Feb. 28, 2018

(86) PCT No.: PCT/EP2018/054966
§ 371 (c)(1),
(2) Date: Aug. 27, 2019

(87) PCT Pub. No.: WO2018/158335
PCT Pub. Date: Sep. 7, 2018

(65) Prior Publication Data
US 2020/0009229 A1 Jan. 9, 2020

(30) Foreign Application Priority Data
Feb. 28, 2017 (EP) .................................... 17158471

(51) Int. Cl.
| | |
|---|---|
| A61K 38/20 | (2006.01) |
| A23K 20/10 | (2016.01) |
| A23L 33/18 | (2016.01) |
| A61K 9/19 | (2006.01) |
| C07K 16/12 | (2006.01) |
| A61K 39/00 | (2006.01) |

(52) U.S. Cl.
CPC .............. *A61K 38/20* (2013.01); *A23K 20/10* (2016.05); *A23L 33/18* (2016.08); *A61K 9/19* (2013.01); *C07K 16/1232* (2013.01); *A23V 2002/00* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 7,320,876 B2 * | 1/2008 | Webel | ............ | C12Y 301/03008 435/15 |
| 2003/0148453 A1 * | 8/2003 | Mantyla | ......... | C12Y 302/01003 435/69.1 |
| 2011/0028695 A1 * | 2/2011 | Revets | ....... | A61P 1/04 530/387.3 |
| 2012/0201812 A1 * | 8/2012 | Brige | ............... | A61K 39/39591 424/133.1 |
| 2014/0065145 A1 * | 3/2014 | Debunne | ............. | A61K 9/1652 424/135.1 |
| 2015/0337292 A1 * | 11/2015 | Guenther | ............. | C07K 16/005 506/26 |

FOREIGN PATENT DOCUMENTS

| | | | |
|---|---|---|---|
| CN | 105385705 A * | 3/2016 | |
| WO | WO-9003431 A1 * | 4/1990 | ........... C12N 15/815 |
| WO | 0133977 A1 | 5/2001 | |
| WO | 0238770 A1 | 5/2002 | |
| WO | 2007010040 A1 | 1/2007 | |
| WO | 2007039586 A1 | 4/2007 | |
| WO | 2008144763 A2 | 11/2008 | |
| WO | 2014033313 A1 | 3/2014 | |
| WO | 2014145016 A2 | 9/2014 | |

OTHER PUBLICATIONS

Reis et al. Journal of Membrane Science 297 (2007) 16-50.*
Zhang et al. App Microbiol Biotechnol (2014) 98:681-694.*
"VHH nanobody properties". https://www.hybribody.com/contenu/synthetic-vhh-library-menu/take-advantage-of-vhh-antibody-properties Retrieved Mar. 30, 2022.*
Amino Acid Structures, Codes and Reference Information https://www.promega.com/resources/tools/amino-acid-chart-amino-acid-structure retrieved Mar. 31, 2022.*
Kanojia et al ((2016) The Production of a Stable Infliximab Powder: The Evaluation of Spray and Freeze-Drying for Production. PLoS One 11(10): e0163109. https://doi.org/10.1371/journal.pone.0163109).*
Defintion of "ratio" from Merriam-Webster.com Dictionary, https://www.merriam-webster.com/dictionary/ratio. Accessed Aug. 29, 2022.*
Huyan et al. Iran J Public Health, vol. 44, No. 12, Dec. 2015.*
Anyaogu, et al. "Manipulating the Glycosylation Pathway in Bacterial and Lower Eukaryotes for Production of Therapeutic Proteins." Current Opinion in Biotechnology, vol. 36, 2015, pp. 122-128.
Blanquet, et al. "Living Recombinant *Saccharomyces cerevisiae* Secreting Proteins or Peptides as a New Drug Delivery System in the Gut." Journal of Biotechnology, vol. 110, No. 1, 2004, pp. 37-49.
Choi, Byung-Kwon, et al. "Improvement of N-Glycan Site Occupancy of Therapeutic Glycoproteins Produced in Pichia Pastoris." Applied Microbiology and Biotechnology, vol. 95, No. 3, 2012, pp. 671-682.

(Continued)

*Primary Examiner* — Oluwatosin A Ogunbiyi
(74) *Attorney, Agent, or Firm* — Patent Law Works LLP

(57) ABSTRACT

The present invention relates to the field of recombinant protein production in a host cell. More specifically the invention relates to the field of oral protein delivery. Specifically, the invention provides oral pharmaceutical formulations comprising the culture medium of a recombinant host secreting a recombinant protein. The resulting oral pharmaceutical formulations are useful for the treatment of gastrointestinal and/or buccal disorders. Additionally, the oral pharmaceutical formulations are useful for prophylactic and vaccine purposes.

Figure 1A:
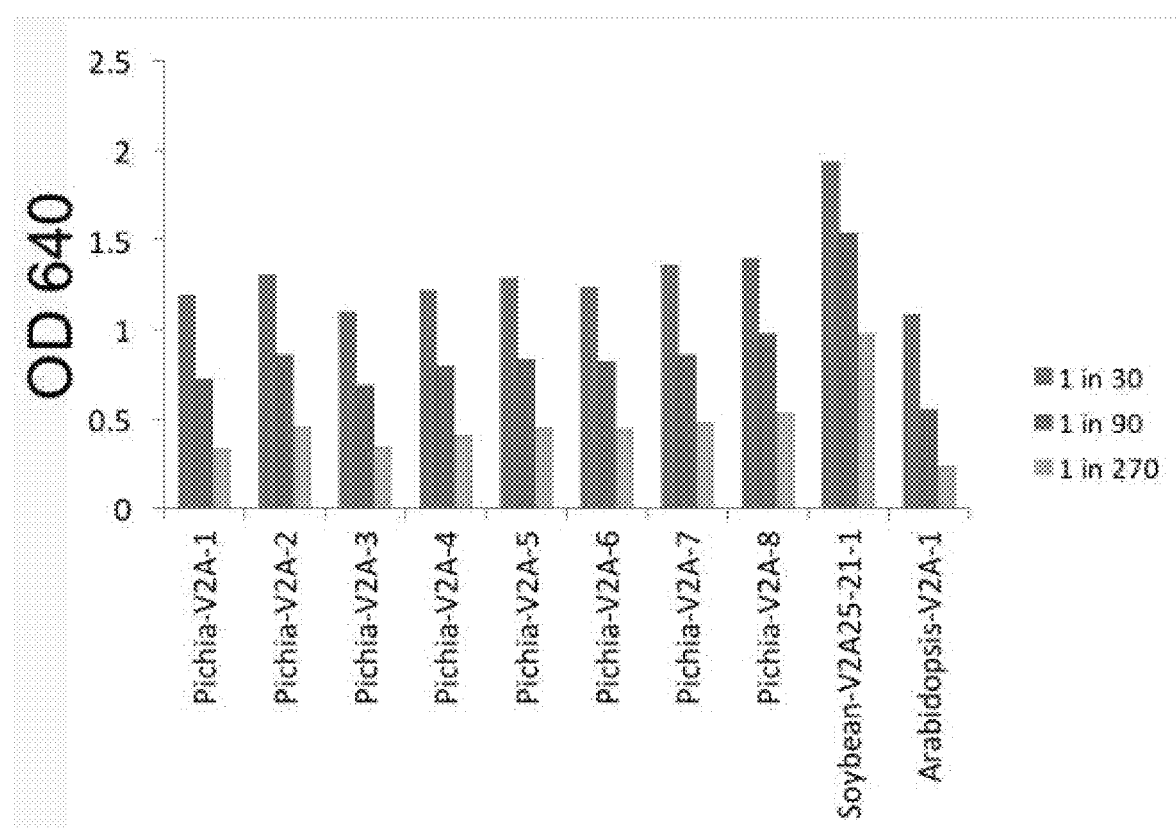
Figure 1B:
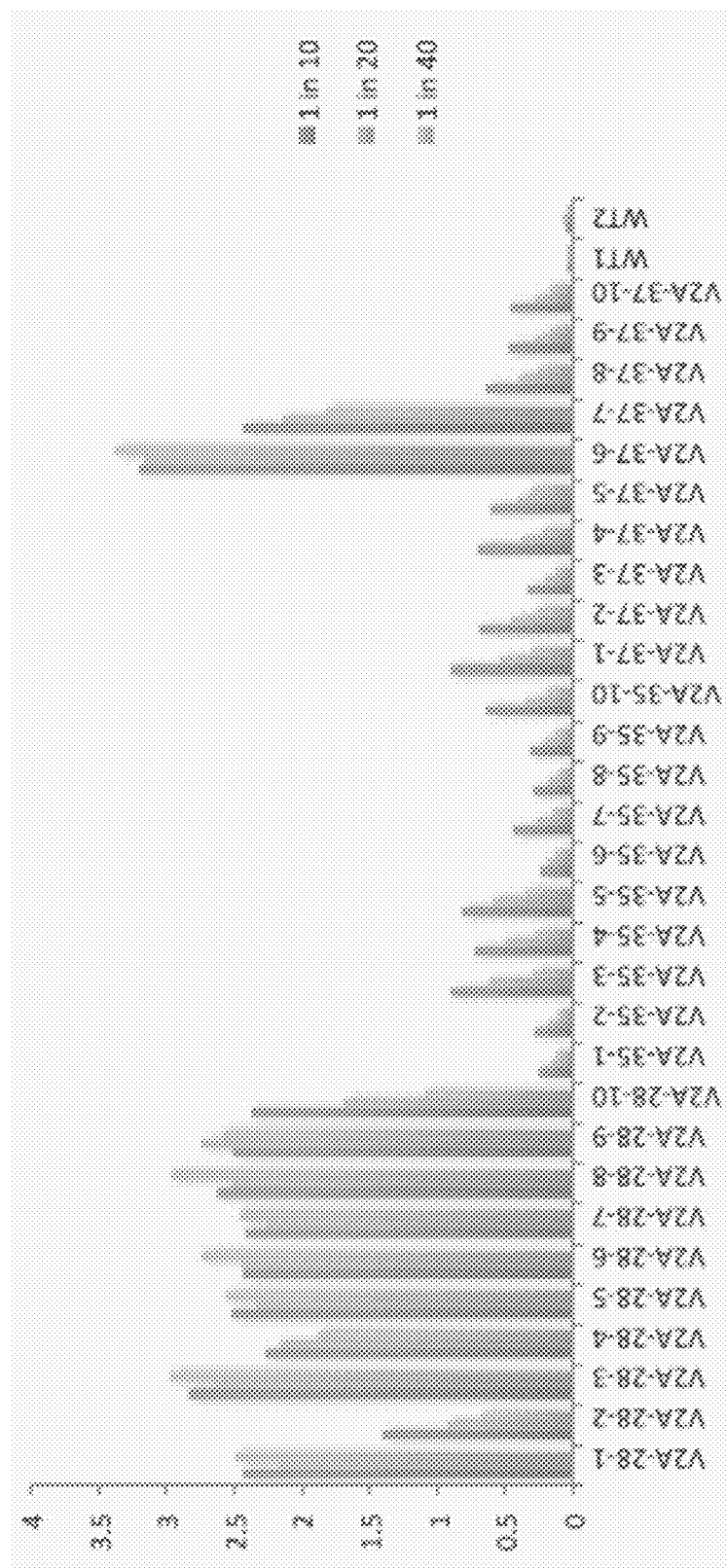
Figure 1C:
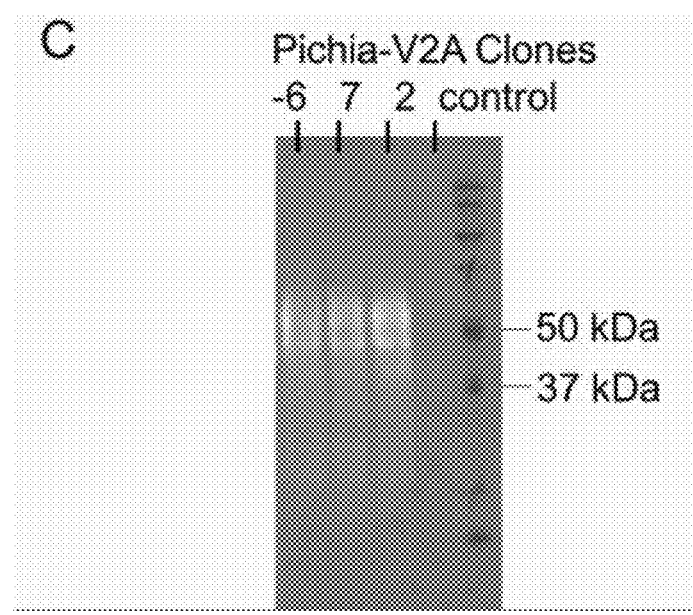
Figure 1D:
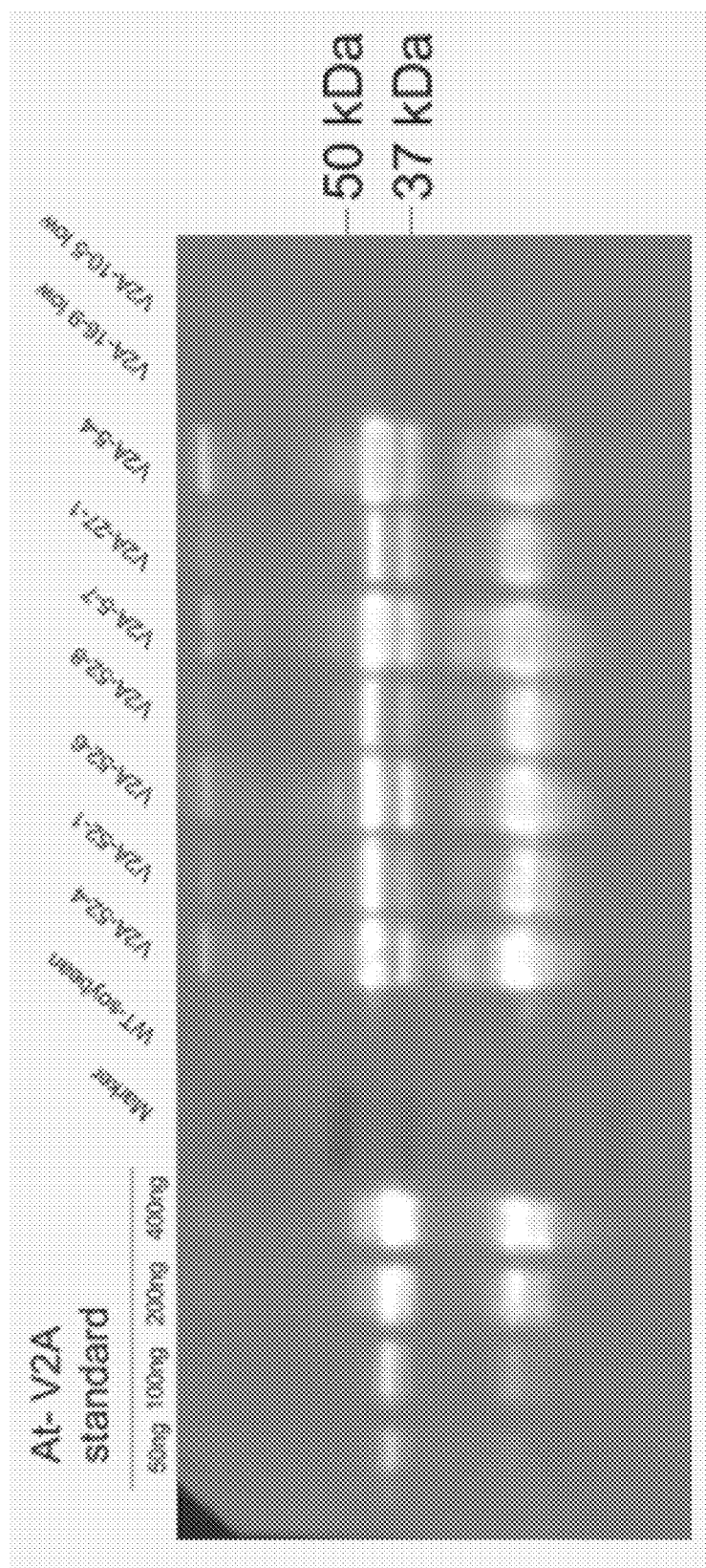

17 Claims, 16 Drawing Sheets
Specification includes a Sequence Listing.

(56) References Cited

OTHER PUBLICATIONS

Ciofalo, et al. "Safety Evaluation of a Lipase Enzyme Preparation, Expressed in Pichia Pastoris, Intended for Use in the Degumming of Edible Vegetable Oil." Regulatory Toxicology and Pharmacology, vol. 45, No. 1, 2006, pp. 1-8.
Farnos, et al. "High-Level Expression and Immunogenic Properties of the Recombinant Rabbit Hemorrhagic Disease Virus VP60 Capsid Protein Obtained in Pichia Pastoris." Journal of Biotechnology, vol. 117, No. 3, 2005, pp. 215-224.
Farnos, Omar, et al. "Biochemical and Structural Characterization of RHDV Capsid Protein Variants Produced in Pichia Pastoris: Advantages for Immunization Strategies and Vaccine Implementation." Antiviral Research, vol. 81, No. 1, 2009, pp. 25-36.
Fingerut, et al. "Vaccine and Adjuvant Activity of Recombinant Subunit B of *E. coli* Enterotoxin Produced in Yeast." Vaccine, vol. 23, No. 38, 2005, pp. 4685-4696.
Garrait, et al. "Genetically Engineered Yeasts as a New Delivery Vehicle of Active Compounds to the Digestive Tract: In Vivo Validation of the Concept in the Rat." Metabolic Engineering, vol. 11, No. 3, 2009, pp. 148-154.
Guan, C, et al. "Expression of Cholera Toxin B-Lumbrokinase Fusion Protein in Pichia Pastoris—The Use of Transmucosal Carriers in the Delivery of Therapeutic Proteins to Protect Rats Against Thrombosis." Applied Biochemistry and Biotechnology, vol. 169, No. 2, 2013, pp. 636-650.
Guan, C., et al. "Bioencapsulation of Living Yeast (*Pichia pastoris*) with Silica After Transformation with Lysozyme Gene." Journal of Solgel Science and Technology. 48.3 (2008): 369-377.
Hamilton, Stephen R., et al. "Production of Sialylated O-Linked Glycans in Pichia Pastoris." Glycobiology, vol. 23, No. 10, 2013, pp. 1192-1203.
Jha, et al. "Protection of Procambarus Clarkii against White Spot Syndrome Virus Using Recombinant Oral Vaccine Expressed in Pichia Pastoris." Fish and Shellfish Immunology, vol. 22, No. 4, 2007, pp. 295-307.
Lee, Chang hoon, et al. "Expression and Characterization of Human Growth Hormone-Fc Fusion Proteins for Transcytosis Induction." Biotechnology and Applied Biochemistry, vol. 46, No. 4, 2007, pp. 211-217.
Li, Xiuying, et al. "Orally Active-Targeted Drug Delivery Systems for Proteins and Peptides." Expert Opinion on Drug Delivery. 11.9 (2014): 1435-1447.
Lu, Ruihua, et al. "Screening, Cloning and Expression Analysis of a Cellulase Derived from the Causative Agent of Hypertrophy Sorosis Scleroteniosis, Ciboria Shiraiana." Gene, vol. 565, No. 2, 2015, pp. 221-227.
PCT International Search Report and Written Opinion, Application No. PCT/EP2018/054966, dated May 25, 2018, 26 pages.
Pietrzak, et al. "An Avian Influenza H5N1 Virus Vaccine Candidate Based on the Extracellular Domain Produced in Yeast System as Subviral Particles Protects Chickens from Lethal Challenge." Antiviral Research, vol. 133, 2016, pp. 242-249.
Rosales-Mendoza, et al. "Food-Grade Organisms as Vaccine Biofactories and Oral Delivery Vehicles." Trends in Biotechnology, vol. 34, No. 2, 2016, pp. 124-136.
Shin, Min-Kyoung, et al. "Animal Vaccines Based on Orally Presented Yeast Recombinants." Vaccine, vol. 31, No. 40, 2013, pp. 4287-4292.
Su, C., et al. "Heterologous Expression of FMDV Immunodominant Epitopes and HSP70 in P. Pastoris and the Subsequent Immune Response in Mice." Veterinary Microbiology, vol. 124, No. 3-4, 2007, pp. 256-263.
Turki, et al. "Preliminary Safety Assessment of Yarrowia Lipolytica Extracellular Lipase: Results of Acute and 28-Day Repeated Dose Oral Toxicity Studies in Rats." Food and Chemical Toxicology, vol. 48, No. 8-9, 2010, pp. 2393-2400.
Virdi, Viikram, et al. "Orally Fed Seeds Producing Designer IgAs Protect Weaned Piglets against Enterotoxigenic *Escherichia coli* Infection." Proceedings of the National Academy of Sciences, vol. 110, No. 29, 2013, pp. 11809-11814.
Wolfe, M. Michael, et al. "Attenuation of Gastric Inhibitory Polypeptide (GIP) Signaling With GIP/FC-IGG Fusion Proteins." Journal of Molecular Neuroscience, vol. 53, No. s1, 2014, p. S170.

\* cited by examiner

Panel A

Panel B

SEQUENCE LISTING

<160> NUMBER OF SEQ ID NOS: 23

<210> SEQ ID NO 1
<211> LENGTH: 41
<212> TYPE: DNA
<213> ORGANISM: Artificial Sequence
<220> FEATURE:
<223> OTHER INFORMATION: Primer

<400> SEQUENCE: 1
ctctctcgag aagagagagg ccgaagctca ggtgcagctg c        41

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
cctcttgagc ggccgccctt tagtagcata tgccttctg          39

<210> SEQ ID NO 3
<211> LENGTH: 48
<212> TYPE: DNA
<213> ORGANISM: Artificial Sequence
<220> FEATURE:
<223> OTHER INFORMATION: Primer

<400> SEQUENCE: 3
gcatcgtctc atcggtctca tatgagattc ccatctattt tcaccgct    48

<210> SEQ ID NO 4
<211> LENGTH: 47
<212> TYPE: DNA
<213> ORGANISM: Artificial Sequence
<220> FEATURE:
<223> OTHER INFORMATION: Primer

<400> SEQUENCE: 4

```
atgccgtctc aggtctcaag aaccaataca agcgttacgc agagaca          47
```

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5

```
gcatcgtctc atcggtctca ttctgtgccg tgcccggtgc cg               42
```

<210> SEQ ID NO 6
<211> LENGTH: 50
<212> TYPE: DNA
<213> ORGANISM: Artificial Sequence
<220> FEATURE:
<223> OTHER INFORMATION: Primer

<400> SEQUENCE: 6

```
atgccgtctc aggtctcagg atccatagca ggtgccatcc acttccgcca       50
```

<210> SEQ ID NO 7
<211> LENGTH: 52
<212> TYPE: DNA
<213> ORGANISM: Artificial Sequence
<220> FEATURE:
<223> OTHER INFORMATION: Primer

<400> SEQUENCE: 7

```
atgcggccgc ttatcacaac tcgtcgtgaa tacaagcgtt acgcagagac at    52
```

<210> SEQ ID NO 8
<211> LENGTH: 50
<212> TYPE: DNA
<213> ORGANISM: Artificial Sequence
<220> FEATURE:
<223> OTHER INFORMATION: Primer

<400> SEQUENCE: 8

```
acaactaatt attgaaagaa ttccgaaacg atgaggcagg tttggttctc       50
```

<210> SEQ ID NO 9
<211> LENGTH: 53
<212> TYPE: DNA
<213> ORGANISM: Artificial Sequence
<220> FEATURE:
<223> OTHER INFORMATION: Primer

<400> SEQUENCE: 9

```
atccagacga caatgagaag aaattggagc agcagaagac acgttgaaaa aac   53
```

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10

```
cgtttcggaa ttctttcaat aattagt                                27
```

<210> SEQ ID NO 11
<211> LENGTH: 24
<212> TYPE: DNA
<213> ORGANISM: Artificial Sequence

```
<220> FEATURE:
<223> OTHER INFORMATION: Primer

<400> SEQUENCE: 11
gctccaattt cttctcattg tcgt                                              24

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
agccaatgca gaggaggc                                                     18

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
gcatcgtctc atcggtctca ttctgtgccg tgcccggtgc cg                           42

<210> SEQ ID NO 14
<211> LENGTH: 50
<212> TYPE: DNA
<213> ORGANISM: Artificial Sequence
<220> FEATURE:
<223> OTHER INFORMATION: Primer

<400> SEQUENCE: 14
atgccgtctc aggtctcagg atccatagca ggtgccatcc acttccgcca                   50

<210> SEQ ID NO 15
<211> LENGTH: 48
<212> TYPE: DNA
<213> ORGANISM: Artificial Sequence
<220> FEATURE:
<223> OTHER INFORMATION: Primer

<400> SEQUENCE: 15
gcatcgtctc atcggtctca tatgagattc ccatctattt tcaccgct                     48

<210> SEQ ID NO 16
<211> LENGTH: 47
<212> TYPE: DNA
<213> ORGANISM: Artificial Sequence
<220> FEATURE:
<223> OTHER INFORMATION: Primer

<400> SEQUENCE: 16
atgccgtctc aggtctcaag aaccaataca agcgttacgc agagaca                      47

<210> SEQ ID NO 17
<211> LENGTH: 45
<212> TYPE: DNA
<213> ORGANISM: Artificial Sequence
<220> FEATURE:
<223> OTHER INFORMATION: Primer

<400> SEQUENCE: 17
gcatcgtctc atcggtctca tatgaggcag gtttggttct cttgg                        45
```

```
<210> SEQ ID NO 18
<211> LENGTH: 50
<212> TYPE: DNA
<213> ORGANISM: Artificial Sequence
<220> FEATURE:
<223> OTHER INFORMATION: Primer

<400> SEQUENCE: 18
gcatcgtctc atcggtctca ttcttgttct ggtccaacac caccaccacc          50

<210> SEQ ID NO 19
<211> LENGTH: 60
<212> TYPE: DNA
<213> ORGANISM: Artificial Sequence
<220> FEATURE:
<223> OTHER INFORMATION: Primer

<400> SEQUENCE: 19
atgccgtctc aggtctcagg atccatagca aataccgtcg ccctcactca taatcacaga  60

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ctcagatcca tgtcctcagt gct                                       23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gaggcagaag gcatatgcta c                                         21

<210> SEQ ID NO 22
<211> LENGTH: 45
<212> TYPE: DNA
<213> ORGANISM: Artificial Sequence
<220> FEATURE:
<223> OTHER INFORMATION: Primer

<400> SEQUENCE: 22
atgccgtctc aggtctcagg atccgtagca tatgccttct gcctc               45

<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
gcatcgtctc atcggtctca ttctgatcca tgtcctcagt gctgc               45
```

MEANS AND METHODS FOR ORAL PROTEIN DELIVERY

FIELD OF THE INVENTION

The present invention relates to the field of recombinant protein production in a host cell such as yeast cells. More specifically the invention relates to the field of oral protein delivery. Specifically, the invention provides oral pharmaceutical formulations comprising the culture medium of a recombinant host secreting a recombinant polypeptide.

INTRODUCTION TO THE INVENTION

Peptides or proteins, including hormones, enzymes, ligands, or inhibitors, including antibodies, regulate various cellular functions. Therefore, they are useful in the clinic to treat or prevent human disorders by modulating physiological or pathological processes. In contrast to small-molecule drugs, the high selectivity of peptides or proteins to their targets may reduce side effects and toxicity to host cell. It is expected that the use of proteins or peptides for therapeutic purposes will continue to increase in the treatment of cancer, metabolic disorders, gastro-intestinal diseases, buccal diseases, neurodegenerative and infectious diseases. Currently, protein drugs are largely manufactured using mammalian, plant, yeast or bacterial cell culture systems. These expressed proteins must be extracted and purified, which requires expensive and complex processes and cold storage and transportation. Biologics are generally delivered by intravenous or subcutaneous injection, which is effective but not desirable for patients, particularly for chronic conditions. Injectable forms of protein drugs often require health care personnel for administration, resulting in frequent hospital visits and decreased patient compliance. Other routes of delivery such as transdermal, intranasal, inhalation and oral administration are under investigation, but oral delivery is generally considered as the most desired route. Despite decades of effort, oral delivery of peptides, proteins and antibody drugs remains a major pharmaceutical challenge, with only a handful of such proteins on the market. This is particularly disappointing since biologics are the fast growing segment of the pharma market, tripling in value from 36 billion dollar to 163 billion dollar in the last 10 years. Thus, while convenient for patients, there exist a number of technical barriers which make this route of administration challenging for large-molecule drugs. Certainly the most important challenge is the enzymatic and pH-dependent degradation of drugs in the stomach and intestines. In addition there is the low permeability of epithelial cells that line the gastrointestinal (GI) tract and the intrinsic instability of these compounds. Several technologies have been developed to facilitate the oral delivery of large molecules. Attaching molecules like polyethylene glycol, an antibody Fc domain or human serum albumin increases peptide stability in serum during circulation. In addition, peptide drugs can be modified to protect from serum proteases and peptidases. Such modifications include N-terminal acetylation, C-terminal amidation, the use of non-natural amino acids, and cyclization via disulfide bonds. In addition, some improvements have been made in the development of enzyme inhibitors, the use of absorption or permeation enhancers, the formulation of polypeptides in capsules, the application of adhesive polymers that stick to the gut lining and the incorporation of carrier molecules in the formulation. Despite these technologies proteins and peptides typically have extremely low bioavailability of less than 2% when taken by mouth. Recently we showed that plant seed produced antibodies survive the gastric canal and were biologically active in the intestine (see WO2014033313 and Virdi V. et al (2013) PNAS, 110, 29, 11809-11814). Plant production systems though capable of producing high amounts of recombinant proteins, owing to the lengthy and expensive regulatory procedures they would not be the best choice for producing edible vaccines. Lower eukaryotic organisms are more desirable are capable of producing higher amounts of recombinant proteins. It would be an advantage to use lower eukaryotic hosts such as yeasts for the production of therapeutic proteins which can be orally delivered. Lower eukaryotic cells have been described for delivery of therapeutic proteins but only as complete recombinant cells which are capable of producing a therapeutic protein (see for example Zhang et al. (2012) BMC Biotechnology 12:97 and WO2007039586). It would be desirable to be able to use only the culture medium comprising the secreted polypeptide instead of the recombinant yeast itself. Even more desirable it would be important not having to purify the therapeutic polypeptide from the culture medium and to use the culture medium as such.

SUMMARY OF THE INVENTION

In the present invention we surprisingly show that a dried formulation comprising the culture medium of a recombinant yeast, which medium comprises a therapeutic polypeptide and which medium has been treated by a membrane separation process to reduce the concentration of permeate compounds, can be used as an oral delivery formulation. It is shown that the powdered dried culture medium (obtained via lyophilisation or via spray drying) comprising the therapeutic polypeptide is surprisingly protected from degradation in the gut. Furthermore it is also shown that the powdered dried formulation also maintains its biological activity in the gut.

In a first aspect the invention provides a dried formulation comprising the mixture of an orally admissible matrix and the culture medium from a recombinant host, in which culture medium the concentration of soluble permeate compounds has been reduced in a membrane separation process, said host producing an exogenous polypeptide which is secreted into said culture medium.

In yet another specific aspect the invention provides a formulation comprising the culture medium from a recombinant yeast, said yeast producing an exogenous polypeptide which is secreted into said culture medium.

In a second aspect the invention provides a formulation according to aspect 1 wherein the water content of said formulation and soluble molecules with a molecular weight lower than 5 kDa are reduced by concentrating said culture medium in a membrane separation process prior to preparing said formulation.

In a third aspect the invention provides a formulation according to aspect 1 wherein the water content and soluble molecules with a molecular weight lower than 5 kDa are reduced by drying said culture medium prior to preparing said formulation.

In a fourth aspect the invention provides a formulation according to aspect 1 wherein the water content of said formulation and soluble molecules with a molecular weight lower than 5 kDa are reduced by drying said formulation.

In a fifth aspect the invention provides a dried formulation comprising the culture medium of a recombinant host, said host producing an exogenous polypeptide which is secreted into said culture medium.

In a sixth aspect the invention provides a dried formulation according to aspect five wherein said recombinant host is a yeast.

In a seventh aspect the invention provides a dried formulation according to aspects 5 and 6 wherein the exogenous polypeptide is fused to an Fc domain.

In an eight aspect the invention provides a dried formulation according to aspect 7 wherein said Fc domain is an IgA Fc domain.

In a ninth aspect the invention provides a dried formulation according to any one of aspects 5 to 8 wherein said exogenous peptide is a prophylactic or therapeutic peptide or wherein said exogenous peptide is a vaccine or forms part of a vaccine.

In a tenth aspect the invention provides a dried formulation comprising a polypeptide which is exogenous to a recombinant host obtained by secretion of said polypeptide into the culture medium of a recombinant host followed by drying of said culture medium.

In an eleventh aspect the invention provides a dried formulation comprising a fusion polypeptide with an Fc domain obtained by producing said fusion polypeptide into the culture medium of a recombinant host followed by drying of said culture medium.

In a twelfth aspect the invention provides a dried formulation according to aspects 10 or 11 wherein said recombinant host is a prokaryotic host, a plant cell or a fungal cell particularly a filamentous fungus.

In a thirteenth aspect the invention provides a dried formulation according to aspects 10 or 11 wherein said recombinant host is a yeast cell.

In a fourteenth aspect the invention provides a dried formulation according to any one of aspects 5 to 13 wherein said drying is carried out by spray-drying.

In a fifteenth aspect the invention provides a dried formulation according to any one of aspects 5 to 13 wherein said drying is carried out by lyophilisation.

In a sixteenth aspect the invention provides a dried formulation according to any one of aspects 5 to 13 further comprising yeast cells.

In a seventeenth aspect the invention provides a dried formulation according to any one of aspects 5 to 13 further comprising a protein rich meal.

In an eighteenth aspect the invention provides a dried formulation according to any one of aspects 5 to 17 for use as a medicament.

In a nineteenth aspect the invention provides a dried formulation according to any one of aspects 5 to 17 to treat gastro-intestinal diseases.

In a twentieth aspect the invention provides a dried formulation according to any one of aspects 5 to 17 for use to treat buccal diseases.

In twenty-first aspect the invention provides a dried formulation according to any one of aspects 5 to 17 for use as a prophylactic product.

In a twenty-second aspect the invention provides a dried formulation according to any one of aspects 5 to 17 for use as a vaccine.

In a twenty-third aspect the invention provides a dried formulation according to any one of aspects 5 to 17 for use as a functional food product.

In a twenty-third aspect the invention provides a dried formulation according to any one of aspects 5 to 17 for use as a medicinal food product.

In a twenty-fourth aspect the invention provides a food product comprising a dried formulation according to any one of aspects 5 to 17.

In a twenty-fifth aspect the invention provides a dried formulation according to any one of aspects 5 to 17 wherein the polypeptide is an IL22 IgAFc-fusion.

In a twenty-seventh aspect the invention provides an oral pharmaceutical formulation comprising a dried formulation according to any one of aspects 5 to 17 and a pharmaceutical excipient.

In a twenty-eight aspect the invention provides a dried formulation according to any one of aspects 5 to 17 for use as a medicament.

In a twenty-ninth aspect the invention provides an oral pharmaceutical formulation according to aspect twenty-seven for use as a medicament.

FIGURES

FIG. 1: Screening and selection of the high expressing *Pichia* clones (A) and soybean seeds (B) via FaeG immobilised ELISA set up. Panel 'C' and 'D' show a representative immunoblot of *Pichia* VHH-IgAFc containing supernatant and soybean VHH-IgAFc expressing seed extracts, respectively.

Figure 2:
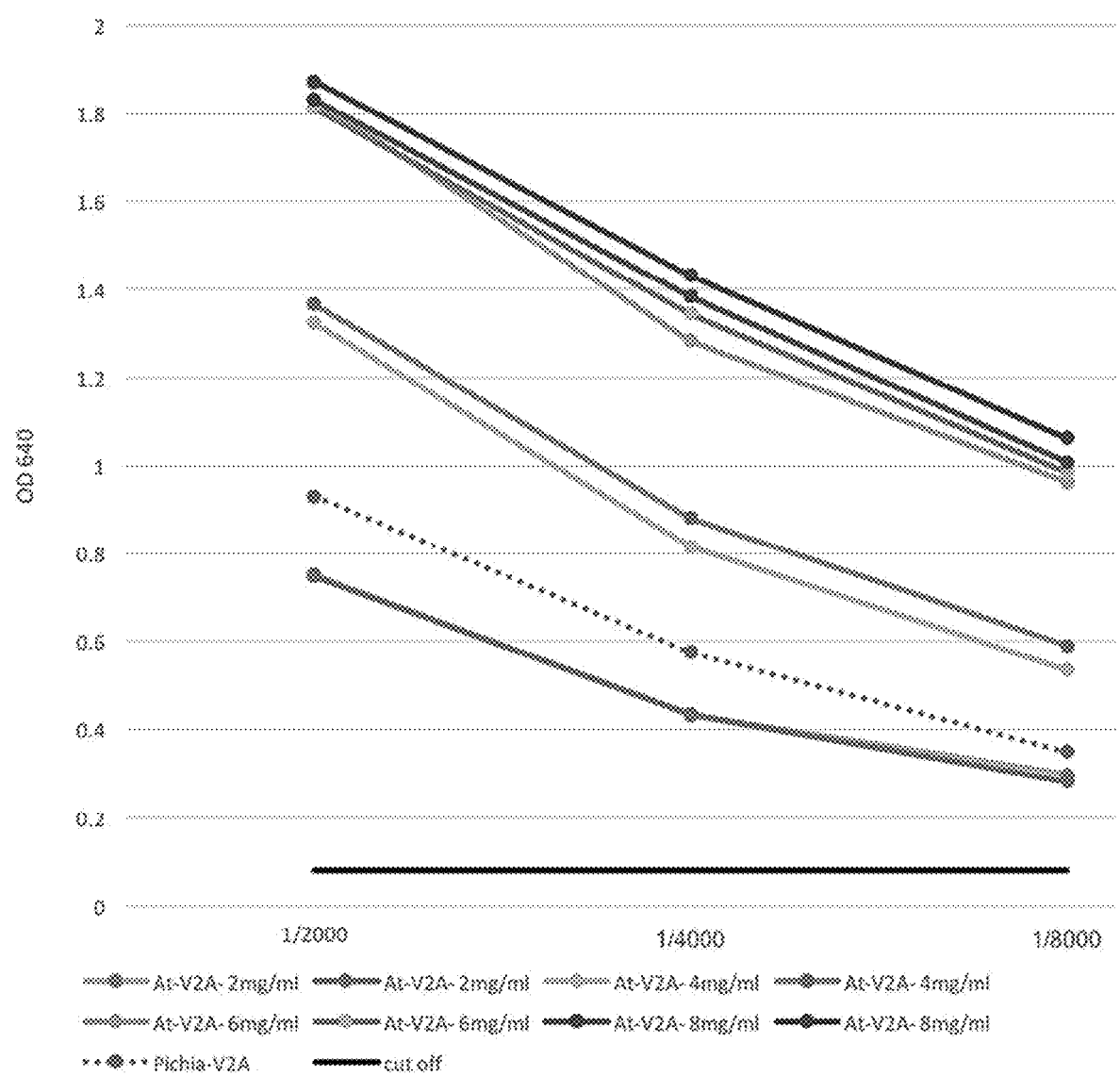

FIG. 2: A typical example of ELISA based titration to compare functional equivalence of *Pichia* and seed produced antibodies. In this representative figure the curve of *Pichia* produced V2A antibody (*Pichia*-V2A), in dotted line, is being compared to different concentrations of *Arabidopsis* produced V2A (At-V2A), solid lines.

FIG. 3: *Pichia* and soybean produced VHH-IgA prevents ETEC infection in piglets. Schematic representation of the experiment (A); Shedding of F4-ETEC post challenge (B); Seroconversion showing anti-F4-ETEC serum IgM (C), IgG (D) and IgA (E) titres.

FIG. 4: Panel A. Experimental set-up of example 3, Panel B. The shedding of F4$^+$ ETEC bacteria per gram of faeces for the 4 different groups until day 6, C. Serum titers of anti-ETEC IgG for individual piglets belonging to the 4 different groups, D. Serum titers of anti-ETEC IgA for individual piglets belonging to the 4 different groups.

Figure 5:
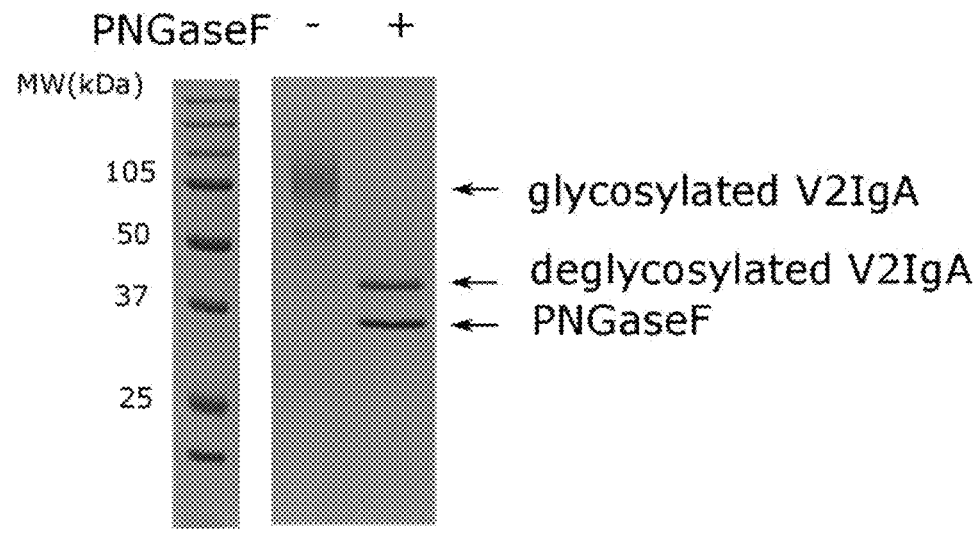
Figure 5:
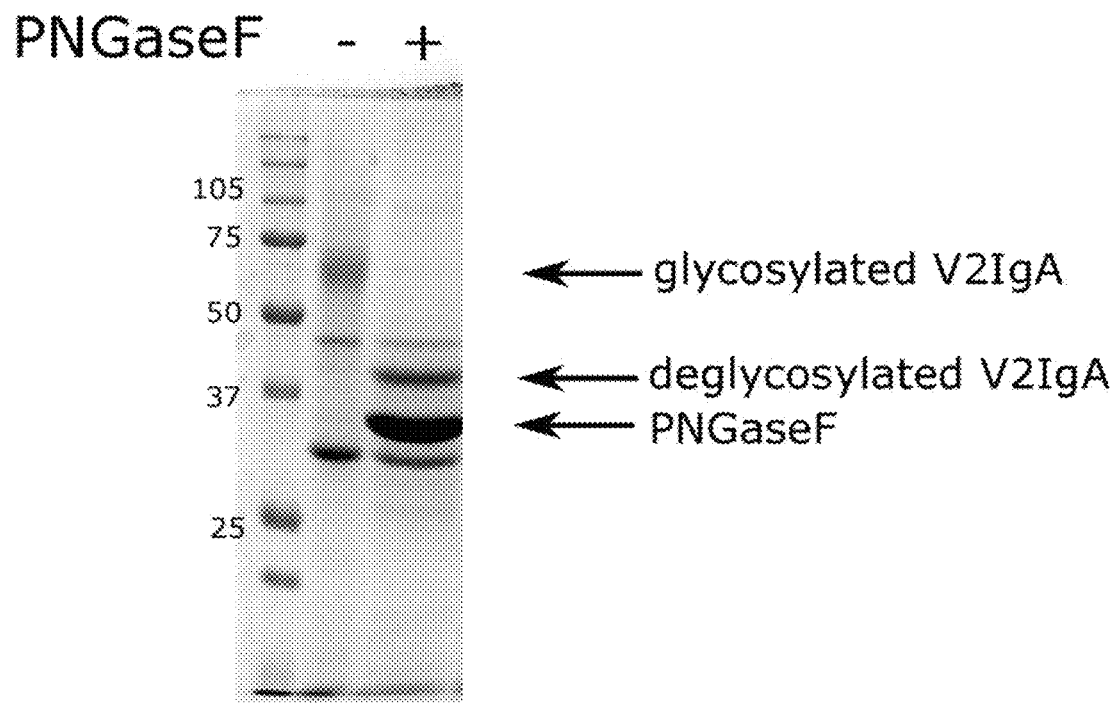

FIG. 5: Reducing SDS-PAGE analysis of GAP promoter driven V2IgAFc-fusion expression produced in *Komagataella phaffi* (formerly known as *Pichia pastoris*). Panel A) C-terminally his tagged V2IgAFc was Ni-IMAC purified and 1 µg of recombinant protein was treated (right lane) or untreated (left lane) with PNGase F; Panel B) crude supernatant of *Komagataella phaffi* producing V2IgAFc was treated (right lane) or untreated (left lane) with PNGase F. Upon PNGase F treatment, the molecular weight is strongly reduced to approximately 38 kDa, which corresponds to the theoretical molecular weight of the unglycosylated molecule. Hypermannosyl structures, present on a single N-glycosylation site add more than 30 kDa to the molecular weight of the protein.

Figure 6:
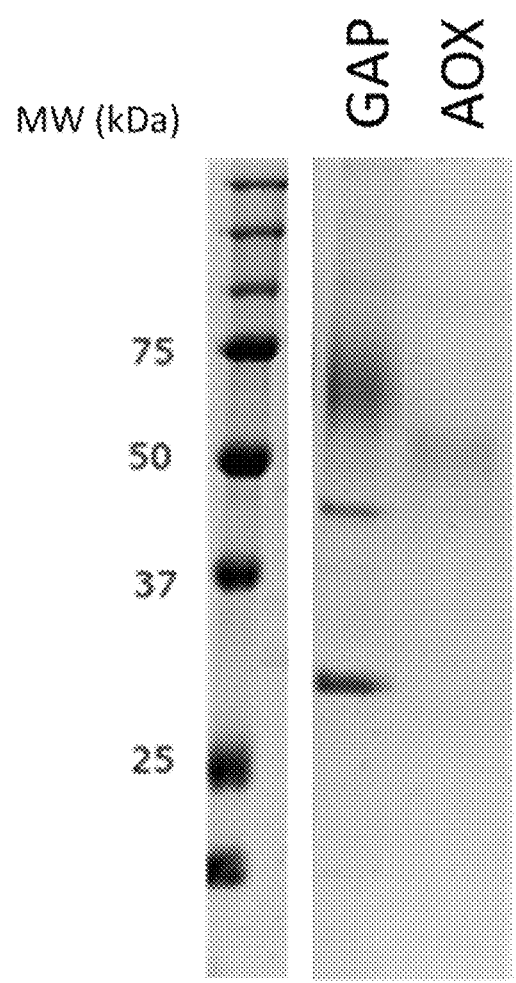

FIG. 6: The glycosylation level is increased when the V2IgAFc molecule is produced in *Komagataella phaffi* from the constitutive GAP promoter (culture on glucose) rather than from the methanol-inducible AOXI promoter (culture on methanol). The average MW of the GAP-promoter produced protein is around 70 kDa, whereas the expected MW for the non-glycosylated V2IgAFc protein would be 38.4 kDa.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Nucleotide sequence", "DNA sequence", "DNA element(s)", or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. "Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A "coding sequence" can include, but is not limited to mRNA, cDNA, recombinant nucleotide sequences or genomic DNA, while introns may be present as well under certain circumstances. "Orthologues" are genes from different organisms that have originated through speciation, and are also derived from a common ancestral gene.

The terms "regulatory element", "control sequence" and "promoter" or "promoter region of a gene" are all used interchangeably herein and are to be taken in a broad context to refer to regulatory nucleic acid sequences that are a functional DNA sequence unit capable of effecting expression of the sequences to which they are ligated. The term "promoter" typically refers to a nucleic acid control sequence located upstream from the transcriptional start of a gene, or is operably linked to a coding sequence, and when possibly placed in the appropriate inducing conditions, is sufficient to promote transcription of said coding sequence via recognition of its sequence and binding of RNA polymerase and other proteins. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. The terms "protein", "polypeptide" and "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes post-translational modifications of the polypeptide, such as glycosylation, phosphorylation and acetylation. By "recombinant polypeptide" is meant a polypeptide made using recombinant techniques, i.e., through the expression of a recombinant or synthetic polynucleotide. The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product. The term "recombinant host cell", "engineered cell", "expression host cell", "expression host system", "expression system" or simply "host cell", as used herein, is intended to refer to a cell into which a recombinant vector and/or chimeric gene construct has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture, cells can be prokaryotic cells, eukaryotic cells such as animal cells, plant cells, fungal cells such as filamentous fungi, preferably a cell is a recombinant yeast cell.

The term "endogenous" as used herein, refers to substances (e.g. genes) originating from within an organism, tissue, or cell. Analogously, "exogenous" as used herein is any material originated outside of an organism, tissue, or cell, but that is present (and typically can become active) in that organism, tissue, or cell.

The gastrointestinal (GI) tract is a hostile environment for polypeptides because it is evolutionarily optimized to break down nutrients and deactivate pathogens. The highly acidic pH in the stomach results in the protonation of proteins and their unfolding, which exposes more motifs that are recognized by protein-degrading enzymes. The enzymes in the stomach (pepsin), small intestine (e.g., chymotrypsin, amino- and carboxypeptidases) and the enzymes produced by the pancreas and bile cleave proteins into smaller fragments and single units. Because therapeutically active polypeptides (e.g. prophylactic, therapeutic of vaccine components) are also affected by these processes, the fraction surviving these degradation processes is generally low and variable, especially in the presence of food. In addition, polypeptide drugs need to overcome multiple barriers designed to prevent the entry of dietary and bacterial antigens in order to reach the systemic compartment. To access the epithelial cell layer, the polypeptide first needs to diffuse through the mucus layer covering the intestinal epithelium. This epithelium is another important barrier, as the tight junctions which seal the epithelial cells restrict the paracellular transport (i.e., the passage between cells) to small molecules and ions smaller than 600 Da. In addition, the passage across the cell is mediated by luminally expressed endocytotic receptors (e.g., vitamin B12 receptor, transferrin receptor), and therefore necessitates conjugation to the respective ligands in order to be exploited in drug delivery. Yet another access point to the systemic compartment is the phagocytotic M-cells of Peyer's patches which sample luminal antigens and can take up particular substrates in the low micrometer range. However, the proportion of M-cells in the gut epithelium is small and varies greatly between species, which complicates predictions of absorption in humans based on animal data. Given the above outlined hurdles it is not surprisingly that only six biomacromolecules have been approved by the Food and Drug Administration (FDA) for oral delivery: two locally and two systemically delivered peptides, one locally delivered non-peptidic macrocycle, and one locally delivered protein mixture (Moroz E. et al (2016) *Advanced Drug Delivery Reviews* 101, 108-121). However, several orally applied formulations of proteins, peptides, and nucleic acids are currently under clinical evaluation. Often, these formulations contain at least one of the following excipients: an enteric coating and/or protease inhibitors to prevent drug degradation and permeation enhancers to enable paracellular transport of macromolecules. Mechanistically, absorption enhancement can be achieved by mechanically disrupting tight junctions or the plasma membrane, lowering mucus viscosity, and modulating tight junction-regulating signaling pathways. Additional strategies for the oral delivery of biomacromolecules under clinical development include buccal delivery, utilizing carrier-mediated transcytosis, and local delivery to GI targets. The overwhelming majority of currently approved oral drugs and clinical candidates exhibit a molecular weight of <1000 Da. Above this threshold, low bioavailability, inter- and intra-individual variability, food effects, and long-term safety concerns of bioavailability-enhancing excipients remain important challenges of oral delivery despite clear advances in knowledge after nearly 90 years of trial and error.

The present invention provides clear solutions for the shortcomings of the current oral delivery of therapeutic proteins. In the present invention we have surprisingly found that a dried formulation obtained by drying the culture medium comprising a plurality of macromolecules larger than 5 kDa of recombinant yeasts which secrete a therapeutic protein in the culture medium, can be used for oral delivery of the dried formulation. Surprisingly this formulation is not only protected by proteolysis and degradation in the gastrointestinal tract but the therapeutic protein present in the dried formulation is also surprisingly biologically active. Without having to limit the invention to a particular mechanism or action we believe that at least one mechanism is that the yeast extracellular medium acts as a protected film around the therapeutic protein which prevents (or slows down) the proteolysis of the therapeutic protein in the gut. This is different from the situation wherein therapeutic proteins are expressed in plant seeds wherein the dried seed matrix protects the therapeutic protein from degradation (see WO2014033313). Yet another possible mechanism is that the glycosylated therapeutic protein consists of (high) mannose sugar structures only (by nature of expressing it in a recombinant yeast host). These bulky high-mannose structures might also protect the therapeutic peptide from proteolytic degradation in the gut. FIG. 5 depicts the bulky high-mannose glycosylation present on the V2A-IgAFc fusion produced in *Pichia pastoris* which recombinant protein is used in the present examples. The major advantage of our finding is that there is no need for a purification of the therapeutic protein meaning that a formulation comprising the medium as such or a dried formulation comprising multiple macromolecules larger than 5 kDa present in the culture medium (including yeast produced own proteins) and the therapeutic protein present in the culture medium can be used as an oral pharmaceutical product. These advantages are outlined in the following embodiments.

In a specific embodiment the invention provides a dried formulation comprising the culture medium of a recombinant host cell, said host cell producing an exogenous protein which is secreted into the growth medium (or culture medium) of said recombinant host cell. Recombinant host cells can be prokaryotic hosts (e.g. *Lactococcus, Bacillus* and other bacterial hosts), eukaryotic hosts such as plant cells, animal cells, fungal cells in particular filamentous fungal cells and yeast cells. A polypeptide can be a therapeutic peptide, a prophylactic peptide or a peptide which can be used in a vaccine composition.

In another specific embodiment the invention provides a dried formulation comprising the culture medium of a recombinant yeast, said yeast producing an exogenous protein which is secreted into the culture medium. The "culture medium" means the fermentation broth (typically from a high density yeast fermentation broth) without the yeast cells. The "culture medium" is also known as the "growth medium" in the art. Several options exist in the downstream processing to separate the yeast cells from the fermentation broth (also known as fermentation broth clarification techniques) such as for example centrifugation followed by depth filtration, centrifugation followed by filter-aid enhanced depth filtration and also microfiltration techniques. It is clear that the fermentation broth is a very complex soup or solution. Fundamentally, the fermentation broth is the sea of nutrients in which the yeasts grow, reproduce and also secrete the therapeutically relevant polypeptide. The fermentation broth typically contains fermentation nutrient ingredients such as yeast peptones (including yeast extracts), yeast autolysates and inactive yeasts. The content of these products varies in B-vitamins, nucleotides, minerals, alpha-amino nitrogen content and other bioactive compounds.

Several membrane separation processes (with varying membrane pore sizes) are known to the skilled person which can be used to reduce the concentration of soluble permeate components and increase further the concentration of retained compounds (here the recombinant polypeptide of interest). Reverse osmosis or hyperfiltration is a membrane separation process, driven by a pressure gradient, in which the membrane separates the solvent from other components of a solution. The membrane configuration is usually cross-flow. With reverse osmosis, the membrane pore size is very small allowing only very small amounts of very low molecular weight solutes (e.g. 100 MW cut off) to pass through the membranes. Ultrafiltration is another membrane separation process, driven by a pressure gradient, in which the membrane fractionates dissolved and dispersed components of a liquid as a function of their solvated size and structure. The membrane configuration is usually cross-flow. In ultrafiltration, the membrane pore size is larger than in the reverse osmosis process thus allowing some components to pass through the pores with the water. It is a separation/fractionation process using a 10,000 MW cutoff. Diafiltration is another type of ultrafiltration which involves the removal or separation of components (permeable molecules like salts, small proteins, solvents etc.) of a solution based on their molecular size by using micro-molecule permeable filters. Yet another process which is commonly used in the course of protein purification and fractionation is to add a concentration of high salt to the growth medium. Proteins differ markedly in their solubilities at high ionic strength, therefore "salting out" is a very useful procedure to assist in the purification and concentration of proteins present in the growth medium. Ammonium sulfate is an inorganic salt with a high solubility that dissociates into ammonium and sulfate in aqueous solutions. Ammonium sulfate is especially useful as a precipitant because it is highly soluble, stabilizes protein structure, has a relatively low density and is relatively inexpensive.

Therefore in yet another embodiment the invention provides a dried formulation comprising a plurality of macromolecules larger than 5 kDa present in the culture medium of a recombinant fungus, said fungus producing an exogenous polypeptide fused to an Fc domain which is secreted into said culture medium.

In yet another embodiment the invention provides a dried formulation comprising a plurality of macromolecules larger than 10 kDa present in the culture medium of a recombinant fungus, said fungus producing an exogenous polypeptide fused to an Fc domain which is secreted into said culture medium.

In yet another embodiment the invention provides a dried formulation comprising a plurality of macromolecules larger than 15 kDa present in the culture medium of a recombinant fungus, said fungus producing an exogenous polypeptide fused to an Fc domain which is secreted into said culture medium.

In specific embodiments the Fc domain in the dried formulations is an IgA Fc domain.

In specific embodiments the exogenous peptide in the dried formulation is a prophylactic or therapeutic peptide or wherein said exogenous peptide is a vaccine or forms part of a vaccine.

Since it is difficult to define the dried formulations of the invention in terms of its technical and structural features we believe that these formulations are more adequately defined in the claims as "obtainable by" formulations. Therefore in another embodiment the invention provides a dried formulation comprising a protein which is exogenous to yeast obtained by secreting said protein into the culture medium of a recombinant yeast followed by drying of said culture medium. In yet another embodiment the invention provides a dried formulation comprising a therapeutic protein which is exogenous to yeast obtained by secreting said therapeutic protein into the culture medium of a recombinant yeast followed by drying of said culture medium. In yet another embodiment the invention provides a dried formulation comprising a prophylactic protein which is exogenous to yeast obtained by secreting said prophylactic protein into the culture medium of a recombinant yeast followed by drying of said culture medium. In yet another embodiment the invention provides a dried formulation comprising a protein which forms part of a vaccine which is exogenous to yeast obtained by secreting said protein into the culture medium of a recombinant yeast followed by drying of said culture medium. In yet another embodiment the invention provides a dried formulation obtained by adding a plurality of macromolecules larger than 5 kDa present in the culture medium of a recombinant fungal host, such as a filamentous fungus or a yeast cell, to an oral admissible matrix, followed by drying the obtained mixture, said culture medium comprising a secreted polypeptide which is exogenous to said recombinant host.

In yet another embodiment the invention provides a dried formulation comprising the mixture of a culture medium of a recombinant host and an orally admissible matrix, said host producing an exogenous polypeptide which is secreted into said culture medium.

In yet another embodiment the invention provides a dried formulation comprising the mixture of a culture medium of a recombinant host and an orally admissible matrix, said host producing an exogenous polypeptide which is secreted into said culture medium and wherein the water content of said formulation is reduced by concentrating said culture medium prior to preparing said formulation.

In yet another embodiment the invention provides a dried formulation comprising the mixture of a culture medium of a recombinant host and an orally admissible matrix, said host producing an exogenous polypeptide which is secreted into said culture medium and wherein the water content of said formulation is reduced by drying said culture medium prior to preparing said formulation.

In yet another embodiment the invention provides a dried formulation comprising the mixture of a culture medium of a recombinant host and an orally admissible matrix, said host producing an exogenous polypeptide which is secreted into said culture medium and wherein the water content of said formulation is reduced by drying said formulation.

In yet another embodiment the invention provides a dried formulation obtained by adding a plurality of macromolecules larger than 5 kDa present in the culture medium of a recombinant host comprising a secreted polypeptide which is exogenous to said recombinant host to an orally admissible matrix, followed by drying the obtained mixture.

In yet another embodiment the invention provides a dried formulation obtained by adding a plurality of macromolecules larger than 5 kDa present in the culture medium of a recombinant fungal cell such as a recombinant filamentous host or a recombinant yeast cell wherein said culture medium comprises a secreted polypeptide which is exogenous to said recombinant fungal cell, to an orally admissible matrix, followed by drying the obtained mixture.

In yet another embodiment the invention provides a dried formulation obtained by adding a plurality of macromolecules larger than 5 kDa present in the culture medium of a recombinant fungal cell such as a recombinant filamentous host or a recombinant yeast cell wherein said culture medium comprises a secreted polypeptide which is exogenous to said recombinant fungal cell, to an oral admissible matrix, followed by drying the obtained mixture wherein said drying is carried out by spray-drying.

In yet another embodiment the invention provides a dried formulation obtained by adding a plurality of macromolecules larger than 5 kDa present in the culture medium of a recombinant fungal cell such as a recombinant filamentous host or a recombinant yeast cell wherein said culture medium comprises a secreted polypeptide which is exogenous to said recombinant fungal cell, and an oral admissible matrix, followed by drying the obtained mixture wherein said drying is carried out by lyophilization.

An "orally admissible matrix" as defined herein is a product which is used in the food industry as a carrier such for example starch, maltodextrin, soy milk proteins, cellulose, pectin and guar gum. In a particular embodiment the orally admissible matrix is an edible matrix. In another particular embodiment the orally admissible matrix is a soluble food-grade nutrient or a soluble food-grade matrix or a soluble food-grade substance.

Dried Formulations

In many instances, it is advantageous to have the dry protein in a powder format, which facilitates its conversion into capsules, tablets, and thin films. A number of drying methods are available in the art to convert protein solutions into dry powder form. Most drying methods involve removal of solvent by either sublimation such as freeze drying or evaporation such as spray drying and fluidized bed drying or precipitation such as supercritical fluid technology. Among these methods spray drying and freeze drying are by far the most commonly used industrial methods of drying of protein solutions. Lyophilization (an equivalent term is freeze drying) is one processing method for removing moisture from biopharmaceuticals and it can increase the stability, temperature tolerance, and shelf life of these products. Although lyophilization is well established within the industry, it requires expensive equipment that takes up a great deal of space within a production facility. Lyophilization also can take days to complete, and manufacturers that need a powdered product must incorporate a granulation step to the process. Thus, lyophilization can be used to obtain a dried formulation by lyophilizing the yeast fermentation broth after the recombinant yeasts have been removed.

Thus in yet another embodiment the invention provides a method to produce a dried formulation comprising the culture medium of a recombinant yeast wherein a protein is present in said culture medium comprising drying said culture medium by lyophilisation.

Spray drying is an alternative technique for preserving biopharmaceuticals and it is a process whereby a liquid formulation is converted into a dry powder in a single step. The process is typically performed by first atomizing the solution into fine droplets that are then dried quickly in a large chamber by using warm gas. The resulting dry particles are collected with a cyclone. Spray drying exposes biopharmaceuticals to shear stress during the atomization step, which could destabilize labile biopharmaceutical compounds such as proteins. Complex biological molecules are more difficult to spray dry because they are sensitive to high shear stress. The amount of shear stress encountered depends on the type of atomizer and the atomization pressure used. A sonic nozzle that can operate at a relatively low pressure of less than 20 psig, which minimizes the shear stress and allows to process complex biopharmaceuticals is conveniently used. Spray drying has been conducted for a wide variety of biopharmaceuticals such as proteins, enzymes, antibodies, viruses, and bacteria. The process removes water and restricts the biopharmaceutical's mobility, which results in a significantly lowered degradation rate. Thus spray drying can be used to obtain a dried formulation by spray drying the yeast fermentation broth after the recombinant yeasts have been removed.

Thus in yet another embodiment the invention provides a method to produce a dried formulation comprising the culture medium of a recombinant yeast wherein a protein is present into said culture medium comprising drying said culture medium by spray drying.

In particular embodiments dissacharides or surfactants are added to the culture medium before spray drying is conducted. Dissacharides and surfactants are described to prevent aggregation (Broadhead J. et al (1993) *J. Pharm. Pharmacol.* 46 (6) 458-467) and additionally improve the storage capacity of the protein-loaded power (Adler M and Lee G (1999) *J. Pharm. Sci.* 88, 199-208).

In yet another embodiment trehalose and/or sorbitol can be added to the culture medium before spray drying is carried out. It is described that the presence of 30% by weight sorbitol substantially reduces the aggregation of a pharmaceutical protein during spray-drying and also the dry storage stability is improved (Maury M. et al. (2005) *Eur. J. of Pharmaceutics and Biopharmaceutics* 59, 251-261), similar effects are described for trehalose.

Thus in a particular embodiment ultrasonic viscosity reduction is applied before conducting the spray drying process. Ultrasonic viscosity reduction allows for a higher particle loading of the solution, which leads to a reduced volume of liquid that must be evaporated. Ultrasonic viscosity reduction results in reduced energy consumption and higher throughput.

Spray drying is more scalable at lower costs with regards to equipment, facility, and utilities. Furthermore, the cycle time for spray drying is hours instead of days, and thus operational costs can be lower than those for lyophilization.

Food Products

In yet another embodiment the invention provides a food product comprising a dried formulation as described herein before.

In yet another embodiment the invention provides a food product comprising a dried formulation as described herein before wherein the food product is a functional food product.

In yet another embodiment the invention provides a food product comprising a dried formulation as described herein before wherein the food product is a medicinal food product.

Several food products may be prepared according to the invention. A non-limiting list of food products comprise meal replacers, soups, noodles, ice-cream, sauces, dressing, spreads, snacks, cereals, beverages, bread, biscuits, other bakery products, sweets, bars, chocolate, chewing gum, dairy products and dietetic products. A discussion of the latter products and how they can be prepared is presented in U.S. Pat. No. 8,105,592 (page 20, starting on line 62 to page 23, line 35.

In yet another embodiment the invention provides an oral pharmaceutical composition comprising a fungal produced IgAFc fusion protein wherein the protein fused with the IgAFc protein is a prophylactic or therapeutic protein or vaccine component.

In yet another embodiment the invention provides an oral pharmaceutical composition comprising a fungal produced IgAFc fusion protein wherein the protein fused with the IgAFc is an immunoglobuling single variable domain.

In yet another embodiment the invention provides an oral pharmaceutical composition comprising a fungal produced IgAFc fusion protein wherein the protein fused with the IgAFc is a VHH domain.

In yet another embodiment the invention provides an oral pharmaceutical composition comprising a fungal produced IgAFc fusion protein wherein the protein fused with the IgAFc is a VHH domain and wherein the VHH domain contains an artificially introduced N-glycosylation site.

In yet another embodiment the invention provides an oral pharmaceutical composition comprising a fungal produced protein modified with N-glycans and/or O-glycans of which at least 5%, at least 10%, at least 20%, at least 30%, at least 40%, at least 50%, at least 60%, at least 70%, at least 80% or more of the glycoprotein molecular weight is contributed by said N- or O-glycans.

In yet another embodiment the invention provides an oral pharmaceutical composition comprising a fungal produced IgAFc-fusion protein modified with N-glycans and/or O-glycans of which at least 5%, at least 10%, at least 20%, at least 30%, at least 40%, at least 50%, at least 60%, at least 70%, at least 80% or more of the glycoprotein molecular weight is contributed by said N- or O-glycans.

In yet another embodiment the invention provides an oral pharmaceutical composition comprising a fungal produced IgAFc-fusion protein modified with N-glycans and/or O-glycans of which at least 5%, at least 10%, at least 20%, at least 30%, at least 40%, at least 50%, at least 60%, at least 70%, at least 80% or more of the glycoprotein molecular weight is contributed by said N- or O-glycans and wherein the protein fused with the IgAFc is an immunoglobulin single variable domain.

Remarkably the N-glycosylation structure mainly consisting of hypermannosyl structures adds to more than 50% of the molecular weight to the IgAFc-fusion protein which is recombinantly produced in yeast. This is witnessed in FIG. 5 (see the difference between glycosylated V2A-IgAFc fusion and the deglycosylated V2A-IgAFc fusion protein). Also remarkably is that when the IgAFc fusion protein is produced under control of the constitutive GAP promoter in yeast that the hyperglycosylation is even more abundant than when the IgAFc fusion protein is produced under control of the methanol oxidase inducible promoter (AOX promoter) (see FIG. 6).

In yet another embodiment the invention provides a fungal produced IgAFc fusion protein for oral administration use.

In yet another embodiment the invention provides a fungal produced IgAFc fusion protein wherein the protein fused with the IgAFc is an immunoglobuling single variable domain for oral administration use.

In yet another embodiment the invention provides a fungal produced IgAFc fusion protein wherein the protein fused with the IgAFc is a VHH domain for oral administration use.

In yet another embodiment the invention provides a fungal produced IgAFc fusion protein wherein the protein fused with the IgAFc is a VHH domain and wherein the VHH domain contains an artificially introduced N-glycosylation site for oral administration use.

In yet another embodiment the invention provides a fungal produced protein modified with N-glycans and/or O-glycans of which at least 5%, at least 10%, at least 20%, at least 30%, at least 40%, at least 50%, at least 60%, at least 70%, at least 80% or more of the glycoprotein molecular weight is contributed by said N- or O-glycans for oral administration use.

Without limiting the invention to a particular mechanism we believe that the hypermannosylated glycan structures as produced by fungal cells on the recombinant (fusion) protein protect the recombinant protein in the gut so that this hypermannosylated recombinant proteins are suitable for oral delivery.

The term "immunoglobulin single variable domain" (abbreviated as "ISVD"), equivalent to the term "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al (1993) Nature 363: 446-448). The term "VHH domain" has been chosen in order to distinguish these variable domains from the heavy chain variable domains that are present in conventional 4-chain antibodies (which are referred to herein as "V H domains" or "VH domains") and from the light chain variable domains that are present in conventional 4-chain antibodies (which are referred to herein as "VL domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16). "Domain antibodies", also known as "Dabs", "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

In yet another embodiment the invention provides a method to produce a dried formulation comprising the culture medium of a recombinant yeast wherein a protein is present into said culture medium comprising:
  i) cultivating a recombinant yeast comprising a protein and allowing to secrete said protein into the culture medium,
  ii) separating the recombinant yeast cells from the culture medium,
  iii) concentrating said culture medium in a membrane separation process, and
  iv) drying said concentrated culture medium Methods to generate recombinant yeasts are well known in the art. Briefly, expression vectors comprising chimeric genes encoding recombinant proteins are present in a recombinant yeast. The expression vector can be integrated into the genome or can be autonomously replicating in the recombinant yeast. Vectors that integrate into the host chromosome are most widely used because of their mitotic stability in the absence of a selection. However, episomal expression vectors exist for some yeast systems. Expression vectors typically contain a strong yeast promoter/terminator and a yeast selectable marker cassette. Most yeast vectors can be propagated and amplified in *E. coli* to facilitate cloning and as such, also contain an *E. coli* replication origin and ampicillin selectable marker. Finally, many yeast expression vectors include the ability to optionally clone a gene downstream of an efficient secretion leader (for example that of the mating factor or the Ost1 sequence (Fitzgerald I & Glick B S (2014) *Microbial cell factories* 13, 1)) that efficiently directs a heterologous protein to become secreted from the cell. A chimeric gene comprises a promoter operably coupled to a nucleic acid sequence encoding for a signal sequence which is operably coupled to a recombinant gene which encodes a useful polypeptide. A promoter can be a constitutive promoter or an inducible promoter.

In yet another embodiment the invention provides a method to produce a dried formulation comprising the fermentation broth of a recombinant yeast wherein a protein is present into said culture medium comprising:
i) cultivating a recombinant yeast comprising a protein and allowing to secrete said therapeutic protein into the culture medium,
ii) drying said fermentation broth (comprising the recombinant yeast and the culture medium)

In yet another embodiment the invention provides a dried formulation of the invention further comprising yeast cells.

In yet another embodiment the invention provides a dried formulation of the invention further comprising non-recombinant yeast cells.

In yet another embodiment the invention provides a method to produce a dried formulation comprising the culture medium of a recombinant yeast wherein an exogenous protein is present into said culture medium and non-recombinant yeast cells comprising:
i) cultivating a recombinant yeast comprising an exogenous protein and allowing to secrete said protein into the culture medium,
ii) separating the recombinant yeast cells from the culture medium,
iii) concentrating said culture medium in a membrane separation process,
iv) adding non-recombinant yeast cells to the culture medium
v) drying said culture medium In yet another embodiment the invention provides a method to produce a dried formulation comprising the culture medium of a recombinant yeast wherein an exogenous protein is present into said culture medium and non-recombinant yeast cells comprising:
i) cultivating a recombinant yeast comprising an exogenous protein and allowing to secrete said exogenous protein into the culture medium,
ii) separating the recombinant yeast cells from the culture medium,
iii) drying said culture medium,
iv) adding a dried formulation of non-recombinant yeast cells to the dried culture medium obtained in step iii).

In yet another embodiment the invention provides a dried formulation of the invention further comprising a protein rich formulation which is different from the proteins present in the yeast fermentation broth.

In yet another embodiment the invention provides a method to produce a dried formulation comprising the culture medium of a recombinant yeast wherein an exogenous protein is present into said culture medium and a protein rich formulation which is different from the proteins present in the yeast fermentation broth comprising:
i) cultivating a recombinant yeast comprising an exogenous protein and allowing to secrete said protein into the culture medium,
ii) separating the recombinant yeast cells from the culture medium,
iii) adding a protein rich formulation to the culture medium,
iv) drying said culture medium In yet another embodiment the invention provides a method to produce a dried formulation comprising the culture medium of a recombinant yeast wherein a therapeutic protein is present into said culture medium and non-recombinant yeast cells comprising:
i) cultivating a recombinant yeast comprising a therapeutic protein and allowing to secrete said therapeutic protein into the culture medium,
ii) separating the recombinant yeast cells from the culture medium,
iii) drying said culture medium,
iv) adding a dried formulation of a protein rich formulation to the dried culture medium obtained in step iii).

In yet another embodiment the invention provides a dried formulation comprising the culture medium of a recombinant yeast, said yeast producing an exogenous Fc fusion protein which is secreted in the culture medium.

In yet another embodiment the invention provides a dried formulation comprising the culture medium of a recombinant yeast, said yeast producing an exogenous Fc fusion protein which is secreted in the culture medium and wherein said Fc domain is a IgA Fc domain.

Because of the difficulties to structurally describe the dried formulations of the invention in terms of its technical features it is more appropriate to define the dried formulations in the "obtainable by" claim format. Therefore in another embodiment the invention provides a dried formulation comprising an exogenous fusion protein between an Fc domain and a polypeptide obtained by secreting said exogenous protein into the culture medium of a recombinant yeast followed by drying of said culture medium.

Fc Fusions Proteins

A Fc region (fragment crystallisable region) is the tail region of an immunoglobulin that interacts with cell surface receptors called Fc receptors and some proteins of the complement system. According to particularly envisaged embodiments, the Fc region in the Fc fusion protein is a Fc region from an immunoglobulin G (IgG) isotype. This can be any of the IgG subclasses (IgG1, 2, 3, 4 in humans). For IgG, like IgA and IgD isotypes, the Fc region is composed of two identical protein fragments, derived from the second and third constant domains of the antibody's two heavy chains. In another embodiment the Fc part in the fusion protein is derived from an IgA antibody. The "Fc fusion proteins" as used herein are fusion proteins, wherein a Fc region is fused to a protein or peptide. A particular class of Fc containing proteins are Fc containing proteins that can bind an antigen. Examples are antibodies, or fusion proteins wherein a Fc region is linked to a binding moiety (e.g. a nanobody, a Fab region, a F(ab') 2 region). In addition, the invention is not limited to human sequences. For instance, it is possible that the Fc region is that of a mouse, or of a camelid, a rhesus monkey, a dog, a cow, a guinea pig, a sheep, a pig, a goat, a horse, a rat, a rabbit, a cat, or any other mammal. It is even possible that the Fc region is from non-mammalian animals (e.g. a chicken). In specific examples a binding moiety can be a non-antibody scaffold. Non-antibody scaffolds broadly fall into two structural classes, namely domain-sized compounds (at 6-20 kDa molecular weight) and constrained peptides (2-4 kDa). Domain-sized scaffolds include Affibodies, Affilins, Anticalins, Atrimers, DARPins, FN3 scaffolds (e.g. Adnectins and Centyrins), Fynomers, Kunitz domains, Pronectins and OBodies, whereas Avimers, bicyclic peptides and Cys-knots are peptide-related (see Vazquez-Lombardi R et al (2015) Drug Discovery Today 20, 10, 1271 for a comprehensive review).

Pharmaceutical Formulation

In a specific embodiment the dried formulations of the invention may be encapsulated with any available soft- or hard capsule technology to result in a solid oral pharmaceutical dosage form which may further comprise enteric or delayed release coatings.

In yet another aspect the dried formulation can be dissolved in a liquid to obtain an emulsion (see Moreira T C et al (2016) Colloids Surf B. Biointerface 143: 399-405). Thus in a particular aspect the pharmaceutical formulation is a liquid. In one aspect the pharmaceutical formulation according to the present invention is a liquid and comprises less than 10% (w/w) water. In one aspect the pharmaceutical formulation according to the present invention is a liquid and comprises less than 9% (w/w) water. In one aspect the pharmaceutical formulation according to the present invention is a liquid and comprises less than 8% (w/w) water. In one aspect the pharmaceutical formulation according to the present invention is a liquid and comprises less than 7% (w/w) water. In one aspect the pharmaceutical formulation according to the present invention is a liquid and comprises less than 6% (w/w) water. In one aspect the pharmaceutical formulation according to the present invention is a liquid and comprises less than 5% (w/w) water. In one aspect the pharmaceutical formulation according to the present invention is a liquid and comprises less than 4% (w/w) water. In one aspect the pharmaceutical formulation according to the present invention is a liquid and comprises less than 3% (w/w) water. In one aspect the pharmaceutical formulation according to the present invention is a liquid and comprises less than 2% (w/w) water. In one aspect the pharmaceutical formulation according to the present invention is a liquid and comprises less than 1% (w/w) water. In one aspect the pharmaceutical formulation according to the present invention is a liquid and comprises less than 0% (w/w) water.

In certain aspects of the present invention, the pharmaceutical formulation may comprise additional excipients commonly found in pharmaceutical formulations, examples of such excipients include, but are not limited to, antioxidants, antimicrobial agents, enzyme inhibitors, stabilizers, preservatives, flavors, sweeteners and other components as described in *Handbook of Pharmaceutical Excipients*, Rowe et al., Eds., 7th Edition, Pharmaceutical Press (2012), which is hereby incorporated by reference.

These additional excipients may be in an amount from about 0.05-5% by weight of the total pharmaceutical formulation. Antioxidants, anti-microbial agents, enzyme inhibitors, stabilizers or preservatives typically provide up to about 0.05-1% by weight of the total pharmaceutical formulation. Sweetening or flavouring agents typically provide up to about 2.5% or 5% by weight of the total pharmaceutical formulation.

Oral pharmaceutical formulations according to this invention may be formulated as solid dosage forms.

Oral pharmaceutical formulations according to this invention may be formulated as solid dosage forms and may be selected from the group consisting of capsules, tablets, dragees, pills, lozenges, powders and granules.

Oral pharmaceutical formulations according to this invention may be formulated as multiparticulate dosage forms.

Oral pharmaceutical formulations according to this invention may be formulated as multiparticulate dosage forms and may be selected from the group consisting of pellets, microparticles, nanoparticles, liquid or semisolid fill formulations in soft- or hard capsules, enteric coated soft-hard capsules.

In one aspect the oral pharmaceutical formulations may be prepared with one or more coatings such as enteric coatings or be formulated as delayed release formulations according to methods well known in the art.

In one aspect, the pharmaceutical formulation according to the invention Is used for the preparation of a medicament.

The term "surfactant" as used herein refers to any substance, in particular a detergent, that can adsorb at surfaces and interfaces, such as but not limited to liquid to air, liquid to liquid, liquid to container or liquid to any solid.

The term "drug", "therapeutic", "medicament" or "medicine" when used herein refer to an active ingredient used in a pharmaceutical formulation, which may be used in for prophylactic, therapeutic or vaccine applications and thus also refer to what was defined as "macromolecular therapeutic" or "therapeutic macromolecule" or "prophylactic macromolecule" or "vaccine macromolecule" in the present patent application.

Prophylactic/Treatment/Vaccines

The dried formulations of the invention comprising a polypeptide can be used for a variety of diseases, obviously depending on the nature of the peptide. For example when the peptide is a therapeutic peptide then several diseases include—but are not limited to—neurodegenerative disorders, cancer, haematological disorders, immunological disorders, cardiac disorders, liver disorders, respiratory disorders, malabsorption disorders, diabetes, viral infections, fungal infections, bacterial infections, ocular diseases, rare metabolic disorders and hypertension.

In a specific embodiment the invention provides dried formulations of the invention for use in the treatment of gastrointestinal disorders. Non-limiting examples of gastrointestinal disorders comprise irritable bowel syndrome, constipation, haemorrhoids (e.g. internal haemorrhoids), anal fissures, diverticular disease, colon polyps, colon cancer, infectious colitis, ulcerative colitis, Crohn's disease, ischemic colitis, radiation colitis and intestinal mucositis.

In yet another specific embodiment the invention provides dried formulations of the invention for use in the treatment of buccal (or mouth) disorders such as cold sores, canker sores, thrush, leukoplakia, dry mouth, gum, bad breath, dental caries, periodontal diseases (e.g. gingivitis), oral Candidiasis, oral Herpex Simplex virus infections, oral human papillomavirus infections, recurrent apthous ulcers, oral and pharyngeal cancers and oral mucositis.

Therapeutic proteins present in the dried formulations of the invention comprise monoclonal antibodies, growth factors, interleukins and the like. In another aspect the exogenous polypeptides can be used for vaccine purposes. In particular the exogenous polypeptides can be used alone as a vaccine or can form part of a vaccine composition.

Recombinant Yeasts

In a specific embodiment the dried formulations of the invention are yeast species which have acquired the GRAS status. GRAS stands for Generally Regarded as Safe. Yeast which have the GRAS status include yeasts such as *Saccharomyces cerevisiae*, *Pichia pastoris*, *Hansenula polymorpha*, *Yarrowia lipolytica* and *Kluyveromyces lactis*. The production of therapeutic proteins in recombinant yeasts is well known to the person skilled in the art. For the yeast *Pichia pastoris* there is for example the review of Julien C (2006) *BioProcess International*, January, p. 22-31, for *Saccharomyces cerevisiae* there is for example the review of Nielsen J (2013) *Bioengineered* 4:4, 207-211, for *Hansenula polymorpha* there is the review of Cox H. et al (2000) *Yeast*, Volume 16, 13, pp. 1191-1203, for *Kluyveromyces lactis* there is the review of van Ooyen A J J et al (2006) *FEM Yeast Res* 6, 381-392 and for *Yarrowia lipolytica* there is the review of Madzak C et al (2004) *J. Biotechnol.* 109(1-2):63-81.

It is to be understood that although particular embodiments, specific configurations as well as materials and/or molecules, have been discussed herein for engineered recombinant yeast cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

1. Orally Delivered *Pichia* Produced Monomeric VHH-IgAFc Fusions are Efficacious in Preventing F4-ETEC Infection in Piglets The monomeric VHH-IgAFc-fusions, designated as V2A and V3A, which were previously generated and evaluated in *Arabidopsis* seeds (see Virdi et al (2013) 110, 29, 11809-11814), were now also produced in the yeast *Pichia pastoris* and in soybean seeds. Briefly, llama heavy chain-only antibodies (VHHs) were generated against F4$^+$ ETEC fimbriae. Selected F4$^+$ ETEC VHHs were grafted on the codon-optimized part of the porcine IgA$^6$. The resultant VHH-IgAFc fusions are designated as V2A and V3A. The expression levels of the functional VHH-IgAFc fusions were evaluated using ELISA with the F4-ETEC tip adhesion antigen-FaeG coated wells, and detected with anti-pig IgA conjugated to horseradish peroxidase. FIG. 1 shows a typical example of screening of a *Pichia* clone (see FIG. 1A) or soybean seed stocks (see FIG. 1B). Twenty individual colonies were screened for each of the *Pichia* produced antibodies V2A and V3A. Similarly, 10-12 seeds were screened from each of the transformed soybean events. 5 such events were screened for V2A and V3A each. The high expressing seed stocks were retained, and a part of which was also used for raising T3 homozygous seed stocks. The expression level of soybean produced V2A and V3A was calculated to be about 0.2% of seed weight, which was similar to the expression level in *Arabidopsis* seeds. The expression level of the secreted *Pichia* V2A and V3A was as high as 100 mg/L (analysed on SDS-PAGE gels stained with Coomassie blue). However, the ELISA based functional analysis showed that 1 ml of *Pichia* supernatant was equivalent to 1 ml soybean or *Arabidopsis* seeds extract (5 mg of seed) (see FIG. 2). It is likely that the quantification of the *Pichia* produced VHH-IgAFc was hampered due to the shielding via the *Pichia* glycans, in this ELISA set up. Indeed, the immunoblot analysis of *Pichia* supernatant (see FIG. 2C) and soybean seed extracts (see FIG. 1D) shows clear hallmarks of differential glycosylation. *Pichia* VHH-IgAFc migrates higher than 50 k Da (~52 k Da) while soybean produced VHH-IgAFc are less than 50 kDa (~48 kDa) (see FIGS. 1, C-D)

Figure 3A:
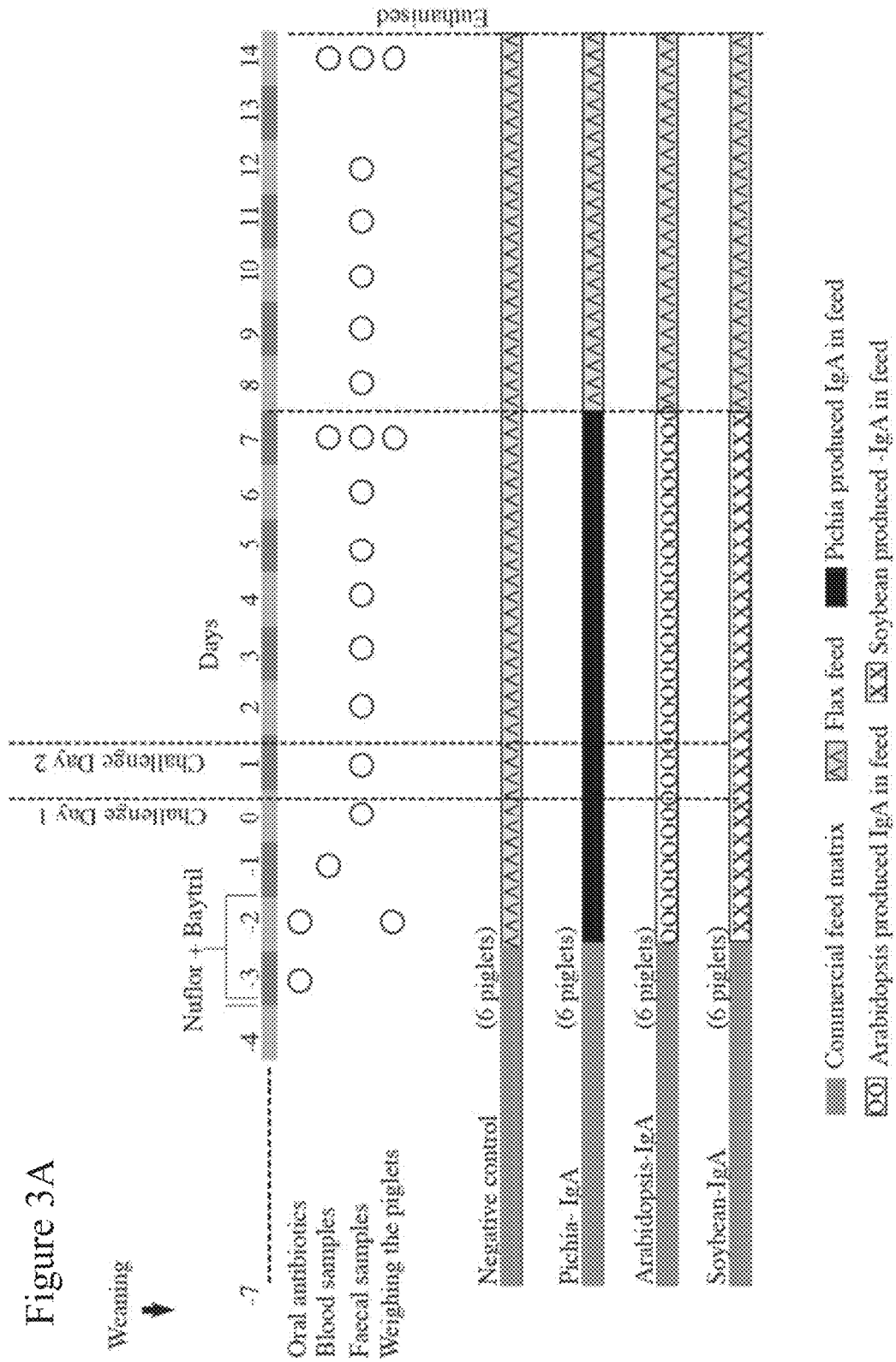
Figure 3B:
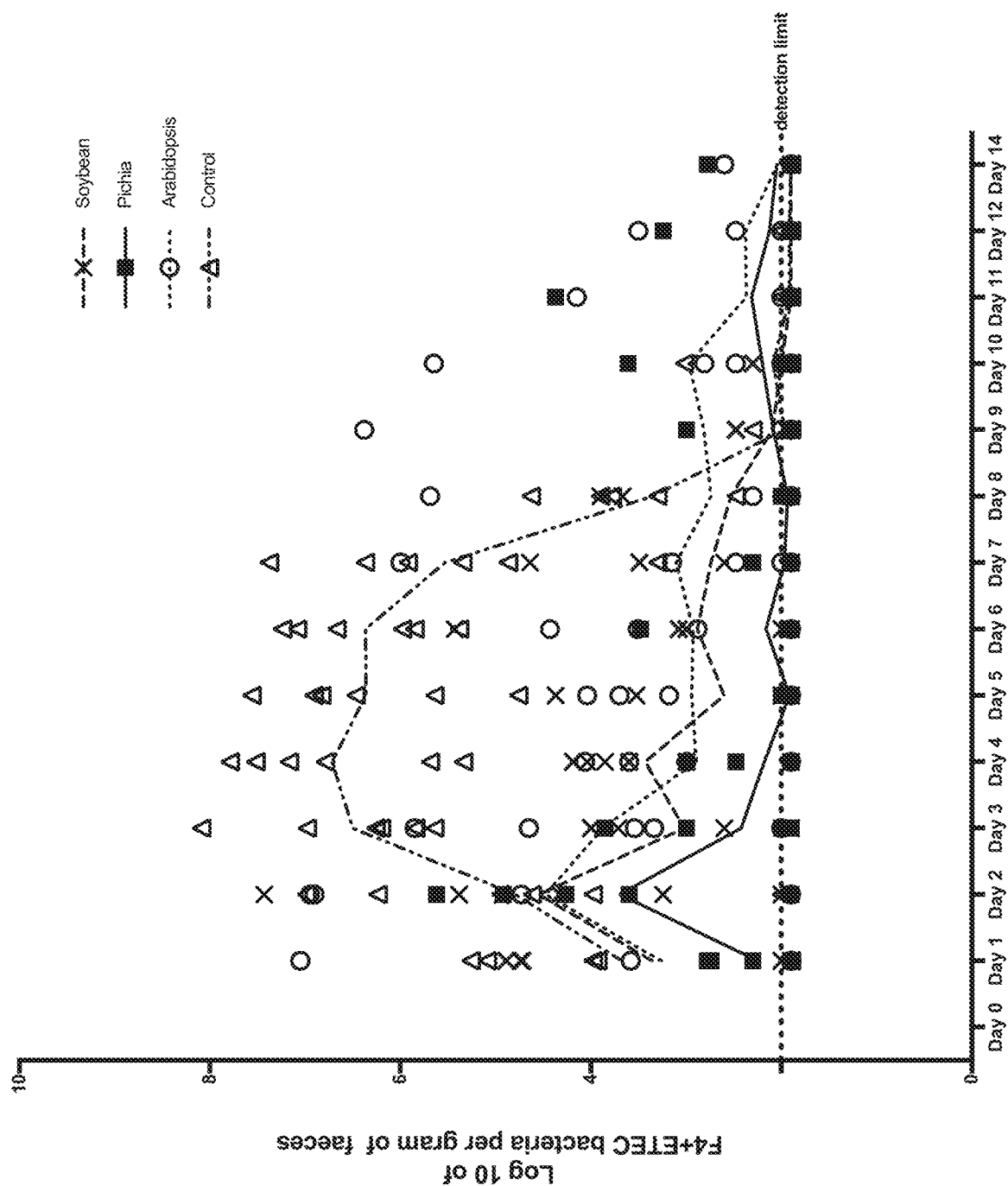
Figure 3C:
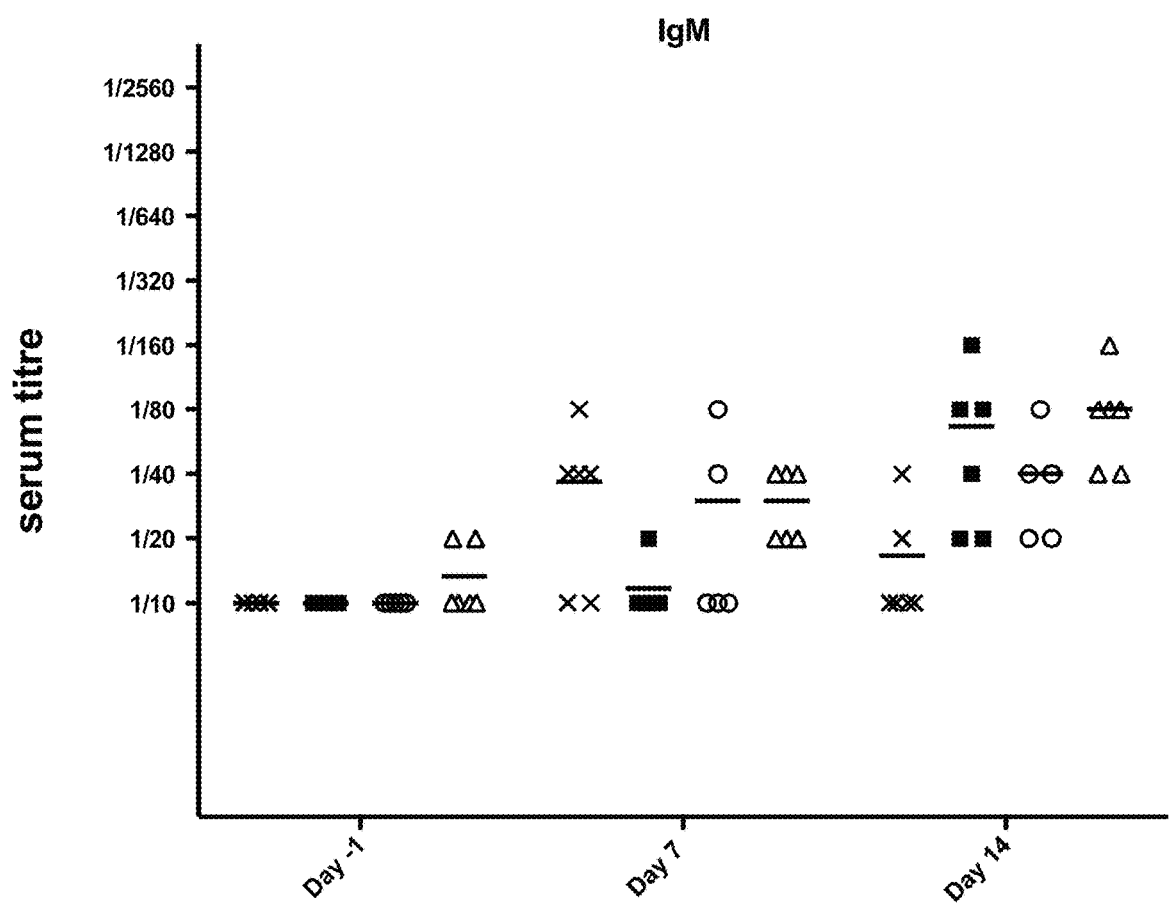
Figure 3D:
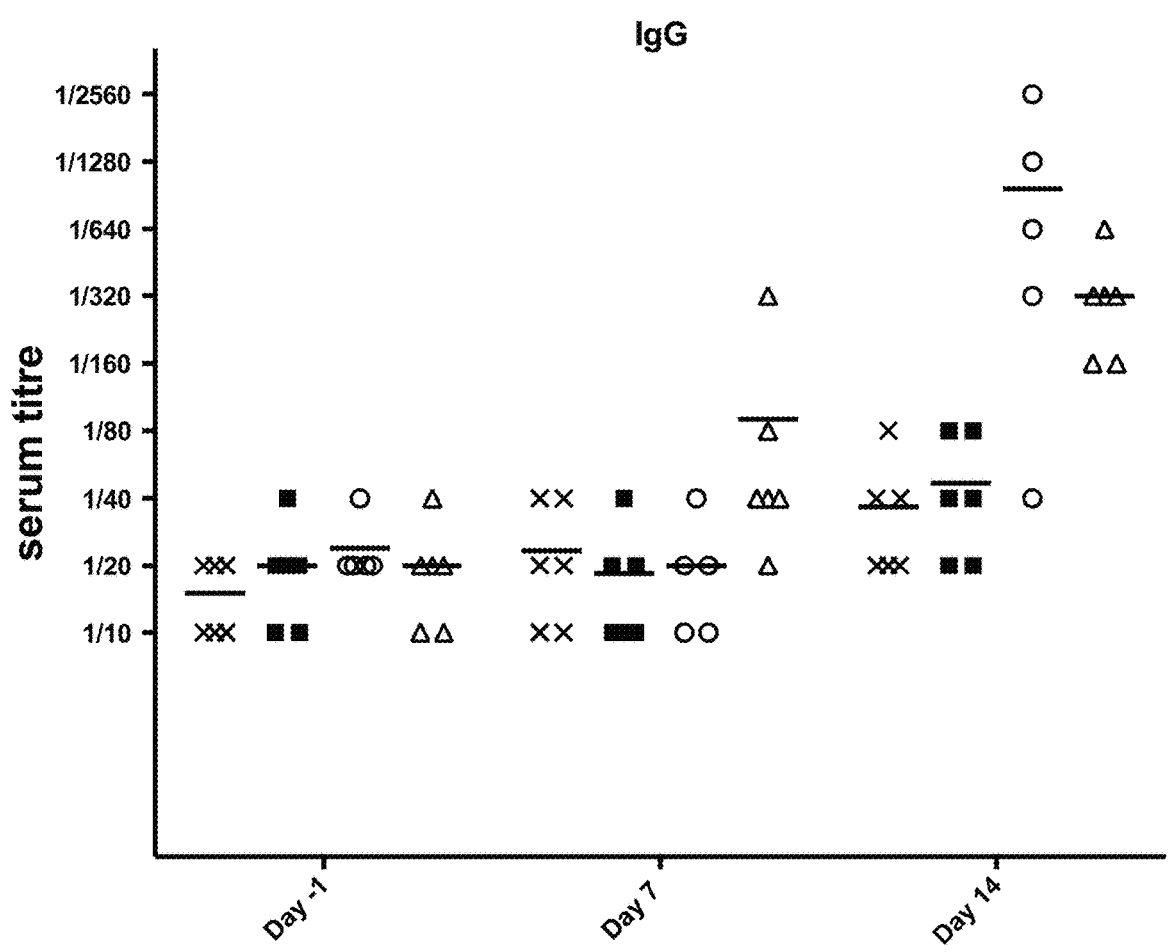
Figure 3E:
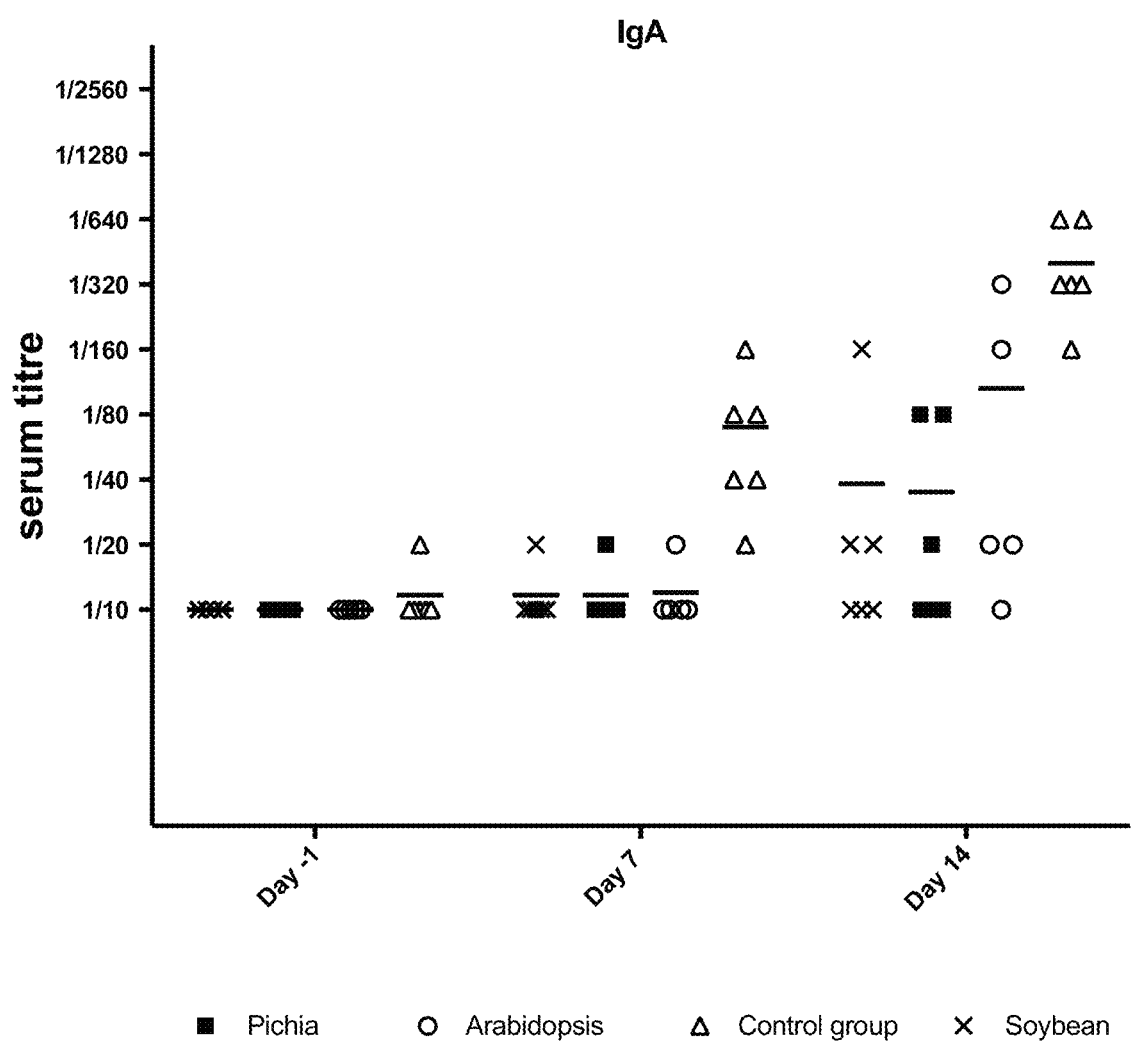

*Pichia* and Soybean Produced VHH-IgAFc Fusions Prevents ETEC Infection in Piglets The in vivo efficacy of *Pichia* and soybean seed produced VHH-IgAFc antibody cocktail of V2A and V3A (dose 5 mg/pig/day), was evaluated in the piglet feed-challenge experiment. The previously generated *Arabidopsis* produced monomeric VHH-IgAFc (see Virdi et al., 2013) PNAS 110, 29, 11809-11814) served as a reference (*Arabidopsis*-group), while feed containing no antibodies (Flax feed, FIG. 3A) served as negative control. The six F4-ETEC seronegative and F4-receptor (F4R) genotype positive piglets present in each of the groups received the experimental feed for a period of 10 days. On the third day all the piglets were challenged with $10^{10}$ F4-ETEC bacteria for two consecutive days (day 0 and day 1) and the resultant effect of the infection was monitored via analysing the daily shedding of the challenge strain until day 14 (FIG. 3B). The piglets were euthanized on day 14, at which point the F4-ETEC bacteria in the contents of jejunum, ileum and caecum were also determined (Table 1).

TABLE 1

Shedding of the F4-ETEC in faeces ($Log_{10}$) per gram of faeces for each piglet

| | | Day 0 | Day 1 | Day 2 | Day 3 | Day 4 | Day 5 | Day 6 | Day 7 | Day 8 | Day 9 | Day 10 | Day 11 | Day 12 | Day 14 | Day 14-jejunum | Day 14-ileum | Day 14-caecum |
|---|---|---|---|---|---|---|---|---|---|---|---|---|---|---|---|---|---|---|
| Soybean | Pig 1 | — | 2.00 | 3.24 | — | 3.60 | — | — | — | — | — | — | — | — | — | — | — | — |
| | pig 2 | — | — | 2.00 | — | — | — | — | — | — | — | — | — | — | — | — | — | — |
| | pig 3 | — | 4.74 | 4.33 | 3.71 | 4.19 | 4.37 | 5.43 | 4.64 | 3.67 | 2.48 | 2.30 | — | — | — | — | — | — |
| | pig 4 | — | — | 5.38 | 2.60 | 4.04 | — | 2.00 | 2.60 | — | — | — | — | — | — | — | — | — |
| | pig 5 | — | 4.89 | 4.93 | 4.00 | 3.85 | 2.00 | 3.08 | 3.49 | 3.90 | 2.48 | 2.00 | — | — | — | — | — | — |
| | pig 6 | — | 4.72 | 7.43 | 4.00 | 3.00 | 3.52 | 3.00 | — | — | — | 2.00 | — | — | — | — | — | — |
| *Pichia* | Pig 7 | — | 2.30 | — | — | — | — | — | — | 2.00 | — | — | — | — | — | — | — | — |
| | Pig 8 | — | 2.78 | — | — | — | — | — | — | — | — | 3.61 | 4.37 | 3.24 | 2.78 | — | — | 2.78 |
| | Pig 9 | — | — | 4.92 | 3.85 | 2.48 | — | — | — | — | — | — | — | — | — | — | — | — |
| | Pig 10 | — | — | 5.62 | 3.00 | — | — | — | — | — | — | — | — | — | — | — | — | — |
| | Pig 11 | — | 2.74 | 4.26 | — | — | — | — | — | — | — | — | — | — | — | — | — | — |
| | Pig 12 | — | — | 3.60 | 2.00 | 3.00 | 2.00 | 3.48 | 2.30 | 2.00 | 3.00 | 2.00 | — | — | — | — | — | — |
| *Arabidopsis* | Pig 13 | — | — | — | 3.34 | — | 3.18 | 3.51 | 6.00 | 5.69 | 6.38 | 5.65 | 4.15 | 2.48 | — | — | — | — |
| | Pig 14 | — | — | — | 5.85 | 3.60 | 4.04 | 4.43 | 3.15 | 2.30 | 2.00 | 2.00 | — | — | — | — | — | — |
| | Pig 15 | — | 3.58 | 4.73 | 2.00 | — | 3.70 | — | 2.48 | — | — | 2.81 | — | 3.50 | 2.60 | — | — | 4.32 |

TABLE 1-continued

Shedding of the F4-ETEC in faeces ($Log_{10}$) per gram of faeces for each piglet

|  |  | Day 0 | Day 1 | Day 2 | Day 3 | Day 4 | Day 5 | Day 6 | Day 7 | Day 8 | Day 9 | Day 10 | Day 11 | Day 12 | Day 14 | Day 14-jejunum | Day 14-ileum | Day 14-caecum |
|---|---|---|---|---|---|---|---|---|---|---|---|---|---|---|---|---|---|---|
| Control | Pig 16 | — | 7.05 | 6.95 | 4.65 | 3.00 | — | — | — | — | — | — | 2.00 | 2.00 | — | — | — | — |
|  | Pig 17 | — | — | 6.90 | 3.54 | 4.06 | — | 2.88 | 2.00 | — | — | 2.48 | — | 2.00 | — | — | — | 2.00 |
|  | Pig 18 | — | — | — | — | — | — | — | — | — | — | — | 2.00 | 2.30 | — | 3.51 | 3.04 | 3.24 |
|  | Pig 19 | — | — | 2.00 | 6.26 | 7.79 | 6.83 | 6.67 | 6.37 | 3.90 | — | — | — | — | — | — | — | — |
|  | Pig 20 | — | 3.98 | 4.62 | 6.20 | 7.52 | 6.91 | 7.08 | 5.92 | 3.30 | — | — | — | — | — | — | — | — |
|  | Pig 21 | — | 3.93 | 6.24 | 8.09 | 7.88 | 7.56 | 7.24 | 7.38 | 3.78 | 2.30 | — | 2.00 | 2.00 | — | — | — | — |
|  | Pig 22 | — | no faeces | 3.98 | 5.64 | 5.69 | 4.76 | 5.98 | 4.87 | 2.48 | — | — | — | — | — | — | — | — |
|  | Pig 23 | — | 5.09 | 6.99 | 5.84 | 6.34 | 5.64 | 5.38 | 5.35 | 4.63 | — | 3.02 | — | — | — | — | — | — |
|  | Pig 24 | — | 5.26 | 4.95 | 6.98 | 6.79 | 6.47 | 5.85 | 3.30 | 2.00 | — | — | — | — | — | — | — | — |

Off note: the post mortem observation revealed that the piglet-18 of the *Arabidopsis*-group, had umbilical-hernia with extreme strangulation of the small intestine resulting in obstructive passage. Hence the data for piglet-18 is not included in the shedding graph (FIG. 3B) or in the statistical analysis (the data is reported in table 1).

Also after euthanasia, the F4-ETEC adhesion assay performed using the intestinal villous enterocytes showed 41 to 85 bacteria bound per 250 µm of the cell surface, dually confirming the phenotypic expression of a high number of F4-receptors (F4R). Hence except the piglet-18, data from all the piglets was used to evaluate the efficacy of monomeric VHH-IgAFc.

The shedding data revealed that the 5 mg/pig per day dose of monomeric VHH-IgAFc V2A and V3A cocktail, produced in *Pichia*, *Arabidopsis* seeds or soybean seeds successfully prevented the ETEC infection. The VHH-IgAFc receiving groups had a significantly lower shedding (see FIG. 3B, Table 1). The highest average shedding in these three groups was recorded on day 2 with 4.5 ($log_{10}$), 3.7 ($log_{10}$) and 4 ($log_{10}$) bacteria per gram of faeces for soybean, *Pichia* and *Arabidopsis* groups, respectively. The shedding declined in these three groups the subsequent day by a log. Reaching average shedding on day 5 to 2.6 ($log_{10}$), 2 ($log_{10}$) and 2,7 ($log_{10}$) bacteria per gram of faeces in soybean, *Pichia* and *Arabidopsis* groups, respectively. The shedding in these groups remained low thereafter, often below detectable levels (2 ($log_{10}$) bacteria per gram of faeces) for some of the piglets of these three groups (see Table 1). In contrast, the piglets of the group receiving no antibodies (control-group) in feed had prolonged shedding of high titres of the challenged bacteria, on an average higher than 6.3 ($Log_{10}$) bacteria per gram faeces from day 3 until day 6; and declined thereafter on day 7 (5.3 ($log_{10}$) bacteria per gram faeces) and day 8 (3.3 ($log_{10}$) bacteria per gram faeces) to below detection levels by day 9. The high and prolonged shedding indicates that the challenged strain could effectively establish the infection and successful colonise the small intestine in the control group. Whereas, the in-feed VHH-IgAFc antibody receiving piglets in the *Arabidopsis*-group, *Pichia*-group and the soybean-group, all showed a quick decline in the F4-ETEC immediately after challenge. This shows that the monomeric VHH-IgAFc in these feeds prevented the F4-ETEC from attaching to the enterocytes, colonising and establishing an infection. This is further corroborated by the anti-F4-ETEC seroconversion (see FIG. 3C). Most of the piglets of the *Pichia*, soybean and *Arabidopsis* groups mounted a lower immune response due to limited exposure of the F4-ETEC pathogen to the immune system, while the average titre of anti-F4-ETEC serum IgG, IgM and IgA levels of the control group steadily increased by day 7 and continued to rise by day 14.

The shedding and seroconversion results clearly demonstrate that the in-feed delivery of 5 mg dose of monomeric VHH-IgAFc formulation against F4-ETEC, composed of equal proportions of VHH-IgAFc antibodies—V2A and V3A, either produced in *Arabidopsis*, soybean or *Pichia* is efficacious. Furthermore, in case of *Pichia* produced antibodies, the in vivo efficacy results duly confirm that the processing and formulation of the medium bearing secreted VHH-IgAFcs is suitable to stably incorporate and orally deliver feed-based *Pichia* produced molecules for gastric indications.

Materials and Methods to Example 1

Expression of VHH-IgAFc

*Arabidopsis*: Previously published *Arabidopsis* lines expressing monomeric V2A-IgAFc and V3A-IgAFc fusions (Virdi et al. (2013) PNAS 110, 29, 11809-11814) were scaled up in the greenhouse, to raise ~100 gram of V2A-IgAFc and V3A-IgAFc producing seeds, to formulate the antibody containing feed for the *Arabidopsis*-group in the challenge experiment.

Soybean: The plasmid pEV2A and pEV3A (Virdi et al. (2013) PNAS 110, 29, 11809-11814) bearing the VHH-IgAFc fusion gene for antibody V2A and V3A, respectively were recombined into the pGW43 multisite gateway cassette (Karimi et al. (2002) *Trends Plant Sci* 7, 193-195) bearing the gene conferring phosphinothricin resistance for the selection of transformant using the herbicide Basta®, as per the Gateway® cloning instruction manual (Invitrogen). The resulting expression vectors were named pMXV2A and pMXV3A, were then introduced in to *Agrobacterium* strain EHA101 for transformation of the soybean plants (cultivar Williams 82) using cotyledons as explants according the method described by Paz M M et al. (2006) *Plant Cell Rep.* 25, 206-213) by the Plant Transformation Facility of Iowa State University. The expression of VHH-IgAFc antibodies was evaluated in the T2 seeds of the transformed events, via ELISA with antigen-FaeGac (the tip adhesion of F4-ETEC) coated wells (Virdi et al (2013) PNAS 110, 29, 11809-11814), and detected with polyclonal anti-pig IgA conjugated to horseradish peroxidase (AbD Serotech; AA140P). Ten to twenty seeds from events expressing high amounts of antibody were retained for growing T2 plants while the remaining seeds were used to formulate the soybean produced VHH-IgAFc bearing-diet for the piglet feed-challenge evaluation.

*Pichia*: The VHH-IgAFc fusion gene for VHH-IgAFc V2A and V3A was PCR-amplified using the primer set Alfa-V2 (CTCTCTCGAGAAGAGAGAGGCCGAAGC-TCAGGTGCAGCTGC (SEQ ID NO: 1)) and IgA-NotI (CCTCTTGAGCGGCCGCCCTTTAGTAG-CATATGCCTTCTG (SEQ ID NO: 2)), as previously described for VHH-IgG by De Meyer T. et al. (2015) *Plant Biotechnol J* 13, 938-947) these primers bear the restriction site AvaI and NotI, by means of which the antibody gene was cloned in frame with the alpha-mating factor within the pPpT4_Alpha_S expression vector (Naatsaari L. et al., (2012) *PLoS ONE* 7, e39720). The respective expression vectors were linearized using the enzyme PmeI and introduced into *Pichia pastoris* via electroporation (Jacobs P P et al. (2009) Nat Protoc. 4, 58-70). The positive *Pichia* colonies were selected on YPD agar plated with 100 µg/ml of Zeocin® and 300 µg/ml of blasticidin. The expression of 20 individual colonies was analysed in the 24-well system, in 2 ml BMGY (1% yeast extract, 2% peptone, 100 mM potassium phosphate, 1.34% YNB, 1% glycerol, pH 6.0) liquid culture. Wherein post 48 hrs of growth, the liquid medium was replaced with BMMY (1% yeast extract, 2% peptone, 100 mM potassium phosphate, 1.34% YNB, pH 5.7) and spiked with 1% methanol every ~12 hrs. The medium containing the secreted VHH-IgAFc antibodies was typically harvested post 48 hrs of induction in BMMY medium. The expression level was evaluated via ELISA with FaeG coated wells. Clones with high expression were identified and the glycerol-stock was generated.

Piglet Challenge Experiment

The piglet challenge experiments were performed in accordance to the Belgian legislations for animal welfare, upon the approval of Animal Care and Ethics Committee of the Faculty of Veterinary Medicine at Ghent University, Belgium (ethical dossier number EC2015/47). For the experiment with *Pichia* and soybean produced monomeric-IgA the piglets (Belgian landrace X English landrace) were bought from farms of the Institute for Agricultural and Fisheries Research (ILVO), Melle, Belgium, from unvaccinated sows. Blood samples were collected from 2-3 week old piglets to monitor levels of anti-ETEC antibodies in serum (approved by the institutional ethical board of ILVO, dossier number—2016/267). Piglets seronegative for F4-ETEC, and positive for the MUC-13 gene (homozygous and heterozygous dominant), determined via MUC-13 PCR (Goetstouwers et al (2014) *PLoS One* 9, e105013), which correlates with the presence of F4-ETEC receptors (F4R) were selected. Each experimental group consisted of six piglets. After weaning piglets were brought to the faculty stables and properly randomized over the feeding groups based on their litter, genotype and weight. The average starting weight of each group was 7.2 kg. The challenge was performed as previously described (Virdi et al (2013) *Proc Nat Acad Sci USA*. 110, 29, 11809-11814). Briefly, the piglets were challenged on consecutive days with $10^{10}$ F4-ETEC bacteria (strain-GIS26R$^{strep}$), via intragastric intubation under sedation, post neutralisation of gastric pH with bicarbonate buffer for 30 minutes. The first day of challenge is accounted as day 0 in the timeline. The feed containing antibodies was administered for a period of 10 days, starting three days before the challenge (FIG. 3, A). Faecal samples were collected from the day of challenge until day 12 and on the day euthanasia, to monitor the shedding of the F4-ETEC challenged strain GIS26R$^{strep}$, on blood agar plates with streptomycin selection (1 mg/ml). Blood samples were taken to monitor the F4-ETEC specific IgG, IgA and IgM titres on day −1, day 7 and day 14. Specific modification, sample collection and manipulations with the animals are schematically represented in FIG. 3A.

Feed Preparation:

For the seed produced antibodies, the precisely weighed respective seeds (soybean or *Arabidopsis*) were crushed and then mixed with basic pig feed in two steps to ensure thorough homogeneity; first in a small volume resulting in a concentrated premix which was subsequently diluted with more pig feed to prepare the experimental feed (Table 2). The seeds were grinded using the knife-mill (Retsch Grindomix GM200) prior to which the seeds and the grinding chamber were chilled using dry ice. To maintain proportional nutrition in all groups throughout each experiment, flax seeds were used to replace *Arabidopsis* seeds (Table 2). Similarly, to account for the additional soybean proteins, wild-type soybean seeds were added to group other than soybean-IgA group at equal proportion to IgA-producing soybean seeds (Table 2).

TABLE 2

Feed formulation. Star (*) refers to the total weight of pooled dried *Pichia* mix, from four batches of freeze drying slurry, (made from filtered, buffer exchanged *Pichia* media and piglet feed) of each production batch. The inclusion percentage within the total feed is indicated in parenthesis.

|  | Mixing step I Premix composition | | | | Mixing step II experimental feed | | |
| --- | --- | --- | --- | --- | --- | --- | --- |
|  | Antibody | | Soybean | | | | |
|  | bearing seeds/ material Kg | Flax seeds Kg | wild type seeds Kg | pig feed Kg | total premix Kg | feed matrix Kg | total feed Kg |
| *Arabidopsis*-IgA | 0.15 (0.83%) | 0 | 0.15 (0.83%) | 1.7 | 2 | 16 | 18 |
| Soybean-IgA | 0 | 0.15 (0.83%) | 0.15 (0.83%) | 1.7 | 2 | 16 | 18 |
| *Pichia*-IgA | 5.368* | 0.15 (0.83%) | 0.15 (0.83%) | 0.337 | 6 | 12 | 18 |
| Flax-soy feed | 0 | 2.49 (0.83%) | 2.49 (0.83%) | 1.02 | 6 | 294 | 300 |

*Pichia:*

As per the ELISA-based equivalence test (FIG. 2), 1 ml of *Pichia* extract was equivalent to 5 mg of VHH-IgAFc-producing *Arabidopsis* seed powder solubilised in an ml of extraction buffer. Based on this proportion, to dose 5 mg *Pichia* produced VHH-IgAFcs for 6 piglets, for 10 days, the necessary amount of 30 L of *Pichia* medium was produced. The 30 L of *Pichia* culture was made in 4 batches of 7.5 L weekly run, as per the standard expression protocol as above (48 hrs growth in BMGY medium followed by induction for 48 hrs in BMMY medium). At the end of each run, the culture medium was harvested by centrifugation, the cell free supernatant was concentrated via diafilteration to 2-1.5 L and subsequently buffer exchanged with sodium-phosphate buffer (pH 6) with 18.75 mM NaCl, using Centramate™ 500 S tangential flow filtration system (Pall Life Science) fitted with 5 kDa Omega™ centramate filter cassette. To the resultant ~2-1.5 L protein solution containing *Pichia* produced VHH-IgAFc, obtained at the end of each of the four batches, an equal weight of commercial pig feed was added and mixed with a hand-held paddle to avoid any foaming, and the slurry was lyophilised using freeze drying (Epsilon 2-10 D LSC-Martin-Christ, Germany) for 47 hours. The resultant dried powder, termed *Pichia* premix, of the 4 batches in total was 5.368 Kg, which was then mixed with of pig feed to result in 18 Kg of final *Pichia* produced VHH-IgAFc bearing feed (Table 2).

Statistical Analysis:

A linear mixed model was used to model the log 10 transformed bacterial counts measured daily from day 1 till day 10 using the mixed procedure from SAS (Version 9.4 of the SAS System for windows 7 64 bit. Copyright © 2002-2012 SAS Institute Inc. Cary, NC, USA, www.sas.com). Since the detection limit for determining bacterial shedding was 2 ($Log_{10}$) per gram of faeces, missing data was imputed with a value of 1.9 (log 10) when no bacteria were detected. Several structures for the variance-covariance matrix of the residuals were tested based on a saturated mean model (i.e. considering all independent variables as categorical variables and including all interaction effects). Several structures were tested: unstructured, compound symmetry, autoregressive, and banded toeplitz. The best structure was chosen based on AIC values. The fixed effects part of the model contained the main effect of feed group and day and their interaction term. The Kenward-Roger approximation for computing the denominator degrees of freedom for the tests of fixed effects was applied as implemented in SAS. Partial F-test were calculated at each day using the plm procedure. At those days where the partial F-test was significant at the 5% significance level, pairwise comparisons were made. Statistical significances were calculated with Wald tests and adjusted for multiple comparisons using to Tukey's method at each day. Residual diagnostics were carefully examined.

2. Evaluation of IgAFc Fusions with Human IL-22 Produced in *Pichia pastoris*

Materials:

Recombinant Murine TNF (mTNF) was produced in-house in *E. coli* and had a specific activity of $9.46 \times 10^7$ IU/mg.

Animals:

The A20 conditional knockout mice ($A20^{IEC-KO}$) were obtained from Prof Geert van Loo. The $A20^{IEC-KO}$ mice are deficient for A20 in intestinal epithelial cells (IECs) (Vereecke, L. et al. (2010) *J. of Experimental Medicine* 207, 1513-1523). For experimentation, only female 8-12 week old mice were used. Mice were housed in individually ventilated cages at the VIB Inflammation Research Center (IRC) in a specific pathogen-free facility. All experiments on mice were conducted according to institutional, national, and European animal regulations. Animal protocols were approved by the ethics committee of Ghent University.

Feed:

A standard powdered mouse feed (Ssniff®R/M-H Complete feed—Maintenance) was purchased from Bio-Service (The Netherlands). To prepare the IL-22 containing feed, the culture supernatant containing each respective IL-22 format was concentrated via diafilteration and subsequently buffer exchanged with sodium-phosphate buffer (pH 6) with 18.75 mM NaCl, using Centramate™ 500 S tangential flow filtration system (Pall Life Science) fitted with 5 kDa Omega™ centramate filter cassette. For each format, the bio-activity was determined in the concentrate and the volume of each format was set to obtain an equal amount of bioactivity per ml of concentrate. To mix with the feed, an equal weight of the standard powdered rodent feed was added to the IL-22 containing concentrate and mixed. Subsequently, the slurry was lyophilised by freeze drying (Epsilon 2-10 D LSC-Martin-Christ, Germany) for 47 hours. The resultant dried powder is then referred to as *Pichia* rodent premix.

In Vitro Testing:

To test the bioactivity of the different IL-22 formats in the production medium, the medium was sampled and the medium was diluted in sterile PBS prior to performing the bio-assay. To test the retention of the bioactivity of the different IL-22 formats in the dried feed, the feed was dissolved 1:1 (v/v) in PBS. The slurry was then centrifuged at 13.000 g. The upper aqueous phase was transferred to a fresh tube and filter sterilized using low-protein binding 0.22 µm syringe filters (Millipore). The filtrate was then diluted in sterile PBS prior to performing the bio-assay.

Human Colo-205 colon carcinoma cells were ordered from the American Type Culture Collection (ATCC) and cultured according to the guidelines provided in the datasheet. Briefly, the cell line was cultured as semi-adherent cells in RPMI1640 (Gibco) supplemented with 10% Fetal Bovine Serum (FBS) at 37° C. 5% CO 2. For passaging, cells growing in suspension were collected and the adherent cells were trypsinized following standard tissue culture procedures.

To determine bioactivity of IL-22 using the Colo-205 assay, cells were seeded in 96-well U-bottom plates at $3.0 \times 10^5$ cells/mL (100 µl/well). Cells were allowed to adapt for 24 hours prior to stimulating the cells with a dilution series of the IL-22 containing fraction. All stimulations were allowed to proceed overnight. As control, a dilution series of commercially available recombinant hIL-22 (carrier-free) produced *E. coli* (BioLegend) was used. The next day, the plates were centrifuged at 400 g, 10 minutes at 4° C. and the supernatant was collected. The supernatant was assayed for IL-10 using the hIL-10 DuoSet ELISA (R&D systems). The data was analyzed in GraphPad Prism 6. Specific activity was determined based the dose-response curve that was used to determine the EC50.

Experimental Model:

To test the protective effect of IL-22, C57BL/6 $A20^{IEC-KO}$ mice (n=8 per group) were gavaged with 10 ml/kg liquid diet (equivalent to 200 µl) containing an equivalent of 20-, 10-, 5-, 1 µg of each IL-22 format or the equivalent feed without IL-22 as control.

To induce experimental colitis, 1 hour after gavage mice were administered a sublethal dose of 250 µg/kg mTNF intraperitoneally (i.p.). Control mice (Mock) were injected with an equivalent volume of 0.9% NaCl i.p. Body temperature and survival were monitored every hour. In a parallel experiment, mice were euthanized after 4 hours for histological analysis and caspase activity assays.

Histology:

Postmortem, the entire colon was removed from cecum to anus, and the colon length was measured as a marker for inflammation. After measuring, parts from the intestine were removed and fixed in 4% Paraformaldehyde (PFA). After paraffin embedding and sectioning, the tissue was stained with hematoxylin/eosin for histological examination. Apoptosis was analyzed by fluorescence microscopy using an in situ cell death detection kit (Roche) for TUNEL staining, Serum Analysis:

Serum pro-inflammatory cytokines IL-6 and MCP-1 were determined in the serum using the Mouse IL-6 DuoSet ELISA kit (R&D Systems) and Mouse CCL2/JE/MCP-1 DuoSet ELISA kit (R&D Systems) respectively. Alanine aminotransferase activity (ALT) and aspartate aminotransferase activity (AST) were analyzed by routine photometric test on a Hitachi 747 analyzer (Diagnostica, Boehringer Mannheim).

Results:

The mock treated $A20^{IEC-KO}$ mice do not show any phenotypical signs of distress. In contrast, mice that receive TNF-injection show clear symptoms of TNF toxicity, including hypothermia and severe diarrhea as soon as 2 hours after injection. In addition, between 5- and 9 hours after injection of TNF, mice start dying. Mice that receive the intra-gastric treatment with the IL-22 containing feed (IL-22 IgAFc or IL-22) only show a mild decrease in body temperature and do not develop diarrhea. Moreover, none of the mice that are treated with any of the IL-22 formats succumb after the TNF-challenge.

Histologically, mice that are only treated with TNF but do not receive IL-22 have a severe damage to the ileum and jejunum, characterized by extensive epithelial damage and the near complete loss of the crypt-villus structure. In contrast, mice receiving any of the IL-22 formats do not show any signs of damage, clearly maintaining barrier integrity. At the cellular level, TUNEL staining is absent after IL-22 treatment, whereas in mice treated with TNF-only, apoptotic cells are highly abundant in the epithelial lining of the villi in addition to cells that already detached and are found in the intestinal lumen.

We further assess the systemic effects by measuring the pro-inflammatory cytokines IL-6 and MCP-1. The levels of both are comparable for control mice and mice receiving the IL-22 formats, whereas mice treated with TNF-only but that did not receive IL-22 have increased Il-6 and MCP-1 levels. In addition, we also assess liver transaminase levels (AST and ALT) as it has been reported that TNF also affects liver physiology. Indeed, mice treated with TNF have increased levels of AST and ALT in the serum whereas IL-22 treated mice do not show this.

Materials and Methods for Example 2

Strains, Media and Reagents

*Escherichia coli* (*E. coli*) MC1061 or DH5α were used for standard molecular biology manipulations. For plasmid propagation, *E. coli* were cultured in LB broth (0.5% yeast extract, 1% tryptone, and 0.5% NaCl) supplemented with the appropriate antibiotics: 50 μg/mL carbenicillin (Duchefa Biochemie), 50 μg/mL kanamycin (Sigma Aldrich), 50 μg/mL hygromycin B (Duchefa Biochemie) or 50 μg/mL Zeocin® (Life Technologies). All PCR reactions were performed using Phusion high-fidelity polymerase (NEB). PCR reagents such as dNTPs and primers were ordered from Promega and IDT respectively.

The *Pichia pastoris* NRRL-Y 11430 strain (syn. *Komagataella phaffi*) was provided by A. Glieder (Technische Universität Graz, Austria). This strain is referred to as wild-type. Yeast cultures were grown in liquid YPD (1% yeast extract, 2% peptone, 1% D-glucose) or on solid YPD-agar (1% yeast extract, 2% peptone, 1% D-glucose, 2% agar) and selected for by using the appropriate antibiotics: 100 μg/mL Zeocin®, 500 μg/mL geneticin/G418 (Life Technologies) or 300 μg/mL hygromycin B. Bacto yeast extract, Bacto tryptone, Bacto peptone, Bacto agar and Yeast Nitrogen Base (YNB) were purchased from Difco (Beckton Dickinson).

For protein expression, cultures were grown in a shaking incubator (28° C., 225 rpm) in BMGY (1% yeast extract, 2% peptone, 100 mM $KH_2PO_4/K_2HPO_4$, 1.34% YNB, 1% glycerol, pH 5.5). For induction of protein expression, the cells were switched to BMMY (1% yeast extract, 2% peptone, 100 mM $KH_2PO_4/K_2HPO_4$, 1.34% YNB, pH 5.5) containing 1% MeOH. To maintain induction and to compensate for evaporation, cultures were spiked with 1% MeOH every 8-12 hours. At the end of induction, cultures were harvested by centrifugation (1.500 g, 4° C. for 10 minutes). The samples were analyzed immediately or snap-frozen in liquid nitrogen prior to storage at −20° C.

Construction of hIL-22 Expression Vectors

The open reading frame of mature human interleukin-22 (hIL-22, UniProtKB accession Q9GZX6, residue 34-179) was codon optimized for expression in *P. pastoris* using Genscript's proprietary algorithm and ordered synthetically. The hIL-22 coding sequence was cloned in-frame with the *S. cerevisiae* α-mating factor in the pKai61EA-yEGFP expression vector, but without including the EA-repeats (Schoonooghe S et al (2009) *BMC Biotechnology* 9, 70). The final expression vector pKai-hIL22 contains the hIL-22 transgene under control of the strong methanol-inducible AOX1 promoter and has a Zeocin® resistance marker for selection in both bacteria and yeast. As an alternative secretion signal, the *S. cerevisiae* Ost1 sequence (Fitzgerald I and Glick B S (2014) Microbial cell factories 13, 1) was PCR amplified from *S. cerevisiae* genomic DNA using primers Ost1SaccharopAOX1Fw and Ost1SaccharoRv.

Construction of hIL-22-hIgA Fc-6×His Expression Vectors

All constructs were cloned using a modular cloning strategy (MoClo) was employed. This system was developed for *S. cerevisiae* (Lee M E et al (2015) *ACS Synth Biol* 4, 975-986) but was adapted in-house for use in *Pichia*. In brief, the MoClo system makes use of standardized entry vectors to subclone the respective 'parts' of a desired construct. Each part within these vectors are flanked by distinct type-II restriction enzyme sites. By pooling the entry vectors in a single reaction and performing consecutive restriction enzyme digestion and T4 ligation reactions, parts that have compatible ends are allowed to assemble and ligate into a circular plasmid to yield the final expression vector. All entry vectors were generated by pooling equimolar amounts (~20 femtomoles) of both the amplified fragment and the MoClo entry vector pYTK001 or the synthetic but identical vector pPTK081. The standard Modular Cloning ("MoClo") protocols were used and feature the addition of the Type II restriction enzyme BsmBI (1U; NEB), the T4 ligase (1U; NEB) and a 10×T4 ligase buffer (NEB) to the pooled sequences. Twenty-four cycles of 42° C. for 2 min and 16° C. for 5 min were performed in a PCR cycler, followed by a final digestion step at 50° C. for 10 min and a heat denaturation step at 80° C. for another 10 min, before holding at 12° C. indefinitely. The resulting vectors were introduced into *E. coli* MC1061 competent cells which were then plated on LB chloramphenicol medium. As the pYTK001/pPTK081 recipient entry vector features a GFP dropout cassette, green-white screening allowed to distinguish colonies that contain the (correct) plasmid from the green false positive clones. Plasmids were isolated and the sequences of interest were verified by Sanger sequencing, using primers PP001 and PP002.

To engineer a hIL-22 fusion construct with the invariable domains of IgA ($P_{AOX1}$-hIL-22-hIgA_Fc-6×His), the α-MF/Ost1/pre-hIL-22 sequences were amplified by PCR with primers that are compatible with the MoClo system. To make a N-terminal fusion of the hIL-22 sequence to the hIgA sequence, the full α-MF-hIL-22 CDS, Ost1-hIL-22 CDS and pre-hIL-22 CDS were considered as a N-terminal tag or 3a part within the MoClo system. Analogously, the invariable domains of IgA (human, mouse and pig) were considered a Gene of Interest or 3b part.

The MoClo entry vectors carrying the α-MF-hIL-22, Ost1-hIL-22 or pre-hIL-22 were all generated by an initial PCR amplification, using the above mentioned pPpT4_Alpha_S expression vectors as template. Both the α-MF-hIL-22 and pre-hIL-22 sequences were amplified with primers IL-22forentryfw and IL-22forentryry while the Ost1-hIL-22 sequence was amplified with primers IL-22ost1forentryfw and IL-22forentryrv. The PCR fragments were then introduced by BsmBI restriction digestion and T4 ligation into the pYTK001/pPTK081.

The sequence of the Fc region of human IgA (*Homo sapiens*, UniproKB: P01877) and mouse IgA (*Mus musculus*, UniprotKB: P01878) was codon optimized for expression in *P. pastoris* and ordered synthetically as gBlocks at IDT. The human and mouse IgA gBlocks were then amplified with the primers IgAforentryfw and IgAforentryry or IgAmouseforentryfw and IgAmouseforentryrv, to allow modular cloning. The Fc region of the pig IgA (*Sus scrofa*, UniprotKB: K7ZRK0) was amplified from the EV2A vector which was previously generated ((Virdi V et al (2013) *PNAS* 110, 11809) with primers IgApigforentryfwcorrect and IgApigforentryrvnew. All IgA sequences were cloned into the pYTK001/pPTK081 vector as a 'part 3b' in the MoClo system.

The entry vectors were then used to generate expression vectors using the MoClo system. Each expression vector was generated by pooling equimolar amounts (~20 femtomoles) of the following parts (available or will be available at Addgene):

| | | |
|---|---|---|
| Part 1 | Assembly connector: | CONLS |
| Part 2 | Promoter: | $P_{AOX1}/P_{CAT1}$ |
| Part 3a | N-terminal tag: | α-MF-prepro/α-MF-pre/Ost1 - hIL-22 |
| Part 3b | Gene of Interest: | hIgA/mIgA/pIgA |
| Part 4a | C-terminal tag: | 6xHis/6xHis-HDEL |
| Part 4b | Terminator: | AOX1TT |
| Part 5 | Assembly Connector | CONRE |
| Part 6 | Yeast marker | Stuffer (as zeocin resistance works in both bacteria and fungi) |
| Part 7 | Miscellaneous | Stuffer |
| Part 8 | *E. coli* marker + ORI | ZeoR + ColE1 |

Primers Used in Example 2

| Name | Sequence |
|---|---|
| pYTK_IL22Fw | GCATCGTCTCATCGGTCTCATATGAG ATTCCCATCTATTTTCACCGCT (SEQ ID NO: 3) |
| pYTK_IL22Rv | ATGCCGTCTCAGGTCTCAAGAACCAA TACAAGCGTTACGCAGAGACA (SEQ ID NO: 4) |
| pYTK_hIgAFw | GCATCGTCTCATCGGTCTCATTCTGT CGCGTGCCCGGTGCCG (SEQ ID NO: 5) |
| pYTK_hIgARv | ATGCCGTCTCAGGTCTCAGGATCCAT AGCAGGTGCCATCCACTTCCGCCA (SEQ ID NO: 6) |
| IL-22rvHDELnew | ATGCGGCCGCTTATCACAACTCGTCG TGAATACAAGCGTTACGCAGAGACAT (SEQ ID NO: 7) |
| Ost1SaccharopAOX1Fw | ACAACTAATTATTGAAAGAATTCCGA AACGATGAGGCAGGTTTGGTTCTC (SEQ ID NO: 8) |
| Ost1SaccharoRv | ATCCAGACGACAATGAGAAGAAATTG GAGCAGCAGAAGACACGTTGAAAAAA C (SEQ ID NO: 9) |
| pPpT4ASpAOX1Rv | CGTTTCGGAATTCTTTCAATAATTAG T (SEQ ID NO: 10) |
| pPpT4ASIL22noprofw | Phos-GCTCCAATTTCTTCTCATTGT CGT (SEQ ID NO: 11) |
| pPpT4ASIL22noprorv | Phos-AGCCAATGCAGAGGAGGC (SEQ ID NO: 12) |
| IgAforentryfw | GCATCGTCTCATCGGTCTCATTCTgt gccgtgcccggtgccg (SEQ ID NO: 13) |
| IgAforentryrv | ATGCCGTCTCAGGTCTCAGGATCCat agcaggtgccatccacttccgcca (SEQ ID NO: 14) |
| IL-22forentryfw | GCATCGTCTCATCGGTCTCATATGAG ATTCCCATCTATTTTCACCGCT (SEQ ID NO: 15) |
| IL-22forentryrv | ATGCCGTCTCAGGTCTCAAGAACCAA TACAAGCGTTACGCAGAGACA (SEQ ID NO: 16) |
| IL-22ost1forentryfw | GCATCGTCTCATCGGTCTCATATGAG GCAGGTTTGGTTCTCTTGG (SEQ ID NO: 17) |
| IgAmouseforentryfw | GCATCGTCTCATCGGTCTCATTCTTG TTCTGGTCCAACACCACCACCACC (SEQ ID NO: 18) |
| IgAmouseforentryrv | ATGCCGTCTCAGGTCTCAGGATCCAT AGCAAATACCGTCGCCCTCACTCATA ATCACAGA (SEQ ID NO: 19) |
| IgApigfw | CTCAGATCCATGTCCTCAGTGCT (SEQ ID NO: 20) |

| Name | Sequence |
| --- | --- |
| IgApigrvnew | GAGGCAGAAGGCATATGCTAC (SEQ ID NO: 21) |
| IgApigforentryrvnew | ATGCCGTCTCAGGTCTCAGGATCCGT AGCATATGCCTTCTGCCTC (SEQ ID NO: 22) |
| IgApigforentryfwcorrect | GCATCGTCTCATCGGTCTCATTCTGA TCCATGTCCTCAGTGCTGC (SEQ ID NO: 23) |

3. In Vivo Efficacy Comparison of Edible Formulations from Different Drying Processes of *Pichia* Produced VHH-IgA-Fc Fusion Oral and gastric stability is paramount for the biotherapeutics like VHH-IgAFcs to be efficacious in the gastrointestinal tract. The matrix surrounding the antibodies (at the molecular level) and the process of drying very likely plays an important role in protecting VHH-IgAFc antibodies from being digested and rendering ineffective in the gut. Here we set out to evaluate the effect on in vivo efficacy of differentially dried *Pichia* produced VHH-IgAFcs in clearing the F4-ETEC infection, which were-freeze dried together with feed matrix (see example 1) or freeze dried without feed matrix. In addition, we also evaluate spray drying process, which is based on an alternative principle involving heat; wherein matodextrin was used as a matrix/carrier. The three differentially processed feed formulation of *Pichia* produced anti-F4-ETEC VHH-IgAFc (V2A and V3A) composed of the same dose; equivalent of 0.5 L of the fermentate per piglet per day or 5 mg VHH-IgAFcs/day/piglet. The forth group received no VHH-IgAFc antibodies in feed, and served as negative control. Twenty-four F4-ETEC seronegative and muc-13 gene test positive piglets, which correlate to susceptibility to F4-ETEC infection, were selected, weaned and housed into 4 groups of 6 piglets each. These piglets were allowed to acclimatise to solid food, after which they were introduced to the group specific experimental feed (see FIG. 4A). The experimental feed was provided for 10 days, on the third day of which all the piglets were challenged with $10^{10}$ F4-ETEC bacteria for two consecutive days (day 0 and day 1). The resultant effect of the infection, in response to the feed formulations was monitored via analyzing the colony forming units (CFU) of the challenge strain shed daily until day 12 (see FIG. 4B and Table 3) in the faeces.

TABLE 3

The daily shedding of the F4-ETEC (Log10) CFU per gram of faeces for each piglet

| | | Day 0 | Day 1 | Day 2 | Day 3 | Day 4 | Day 5 | Day 6 | Day 7 | Day 8 | Day 9 | Day 10 | Day 11 | Day 12 |
| --- | --- | --- | --- | --- | --- | --- | --- | --- | --- | --- | --- | --- | --- | --- |
| Spray dried | Piglet 1 | — | — | — | — | 2.48 | 2.30 | — | — | — | — | — | — | — |
| | Piglet 2 | Dead | — | | | | | | — | — | — | — | — | — |
| | Piglet 3 | — | — | 6.76 | — | — | — | — | — | — | — | — | — | — |
| | Piglet 4 | — | — | 2.60 | — | — | — | — | — | — | — | — | — | 2.60 |
| | Piglet 5 | — | — | 3.48 | 3.00 | 2.00 | — | — | — | — | 2.00 | — | — | — |
| | Piglet 6 | — | — | — | — | — | — | — | — | — | — | — | — | — |
| Control | Piglet 7 | — | — | 6.68 | 5.07 | — | — | — | — | — | — | — | — | — |
| | Piglet 8 | — | 3.95 | 5.90 | — | — | — | — | — | — | — | — | — | — |
| | Piglet 9 | — | 2.48 | dead | | | | | — | — | — | — | — | — |
| | Piglet 10 | — | 5.68 | 5.00 | — | — | — | — | — | — | — | — | — | — |
| | Piglet 11 | — | 3.48 | 5.16 | 3.00 | 2.48 | — | — | — | — | — | — | — | — |
| | Piglet 12 | — | 4.28 | 3.78 | 2.48 | — | — | — | — | — | — | — | — | — |
| Freeze dry without matrix | Piglet 13 | — | 3.30 | 4.16 | — | — | — | — | — | — | — | — | — | — |
| | Piglet 14 | — | — | — | 3.07 | — | — | — | — | — | — | — | — | — |
| | Piglet 15 | — | — | — | — | — | — | — | — | — | — | — | — | — |
| | Piglet 16 | — | 3.48 | — | — | — | — | — | — | — | — | — | — | — |
| | Piglet 17 | — | 5.47 | 3.18 | — | — | — | — | — | — | — | — | — | — |
| | Piglet 18 | — | 4.00 | 7.04 | 4.99 | 3.85 | 3.43 | 2.48 | 2 | — | — | — | — | — |
| freeze dry with feed matrix | Piglet 19 | — | — | 3.48 | — | — | — | — | — | — | — | — | — | — |
| | Piglet 20 | — | — | — | — | — | — | — | — | — | — | — | — | — |
| | Piglet 21 | — | 3.06 | 4.04 | — | — | — | — | — | — | — | — | — | — |
| | Piglet 22 | — | 3.43 | 4.53 | — | — | — | — | — | — | — | — | — | — |
| | Piglet 23 | — | 2.78 | — | — | — | — | — | — | — | — | — | — | — |
| | Piglet 24 | — | — | — | — | — | — | — | — | — | — | — | — | — |

Note:

The log (10) CFU detection limit is 2, the dash (—) denotes no bacteria was detected Note:

Piglet 2 and piglet 9 died on day −5 and day 2, respectively; due to large gastric ulcers discovered during post-mortem investigation.

Figure 4A:
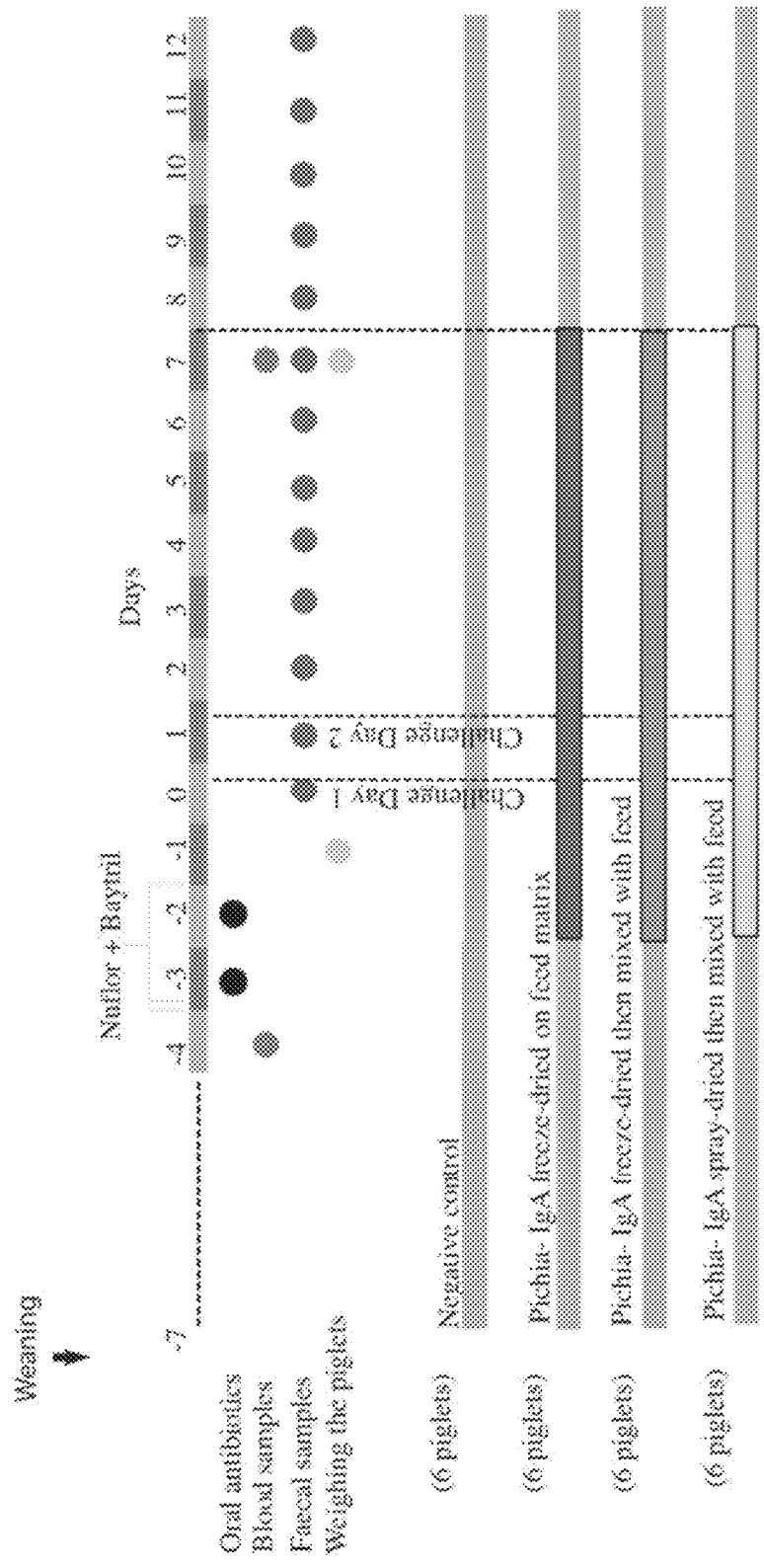
Figure 4B:
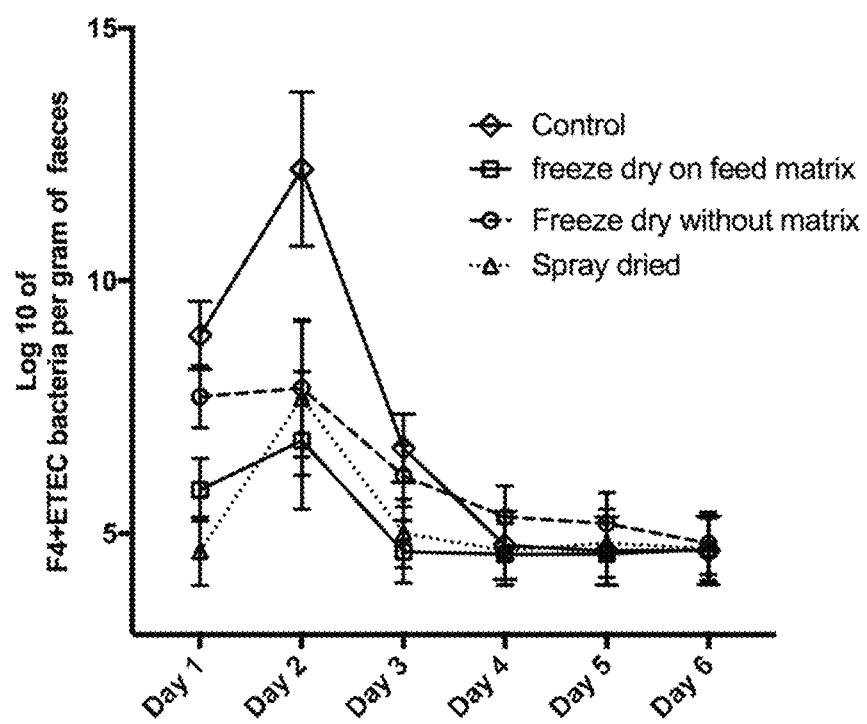
Figure 4C:
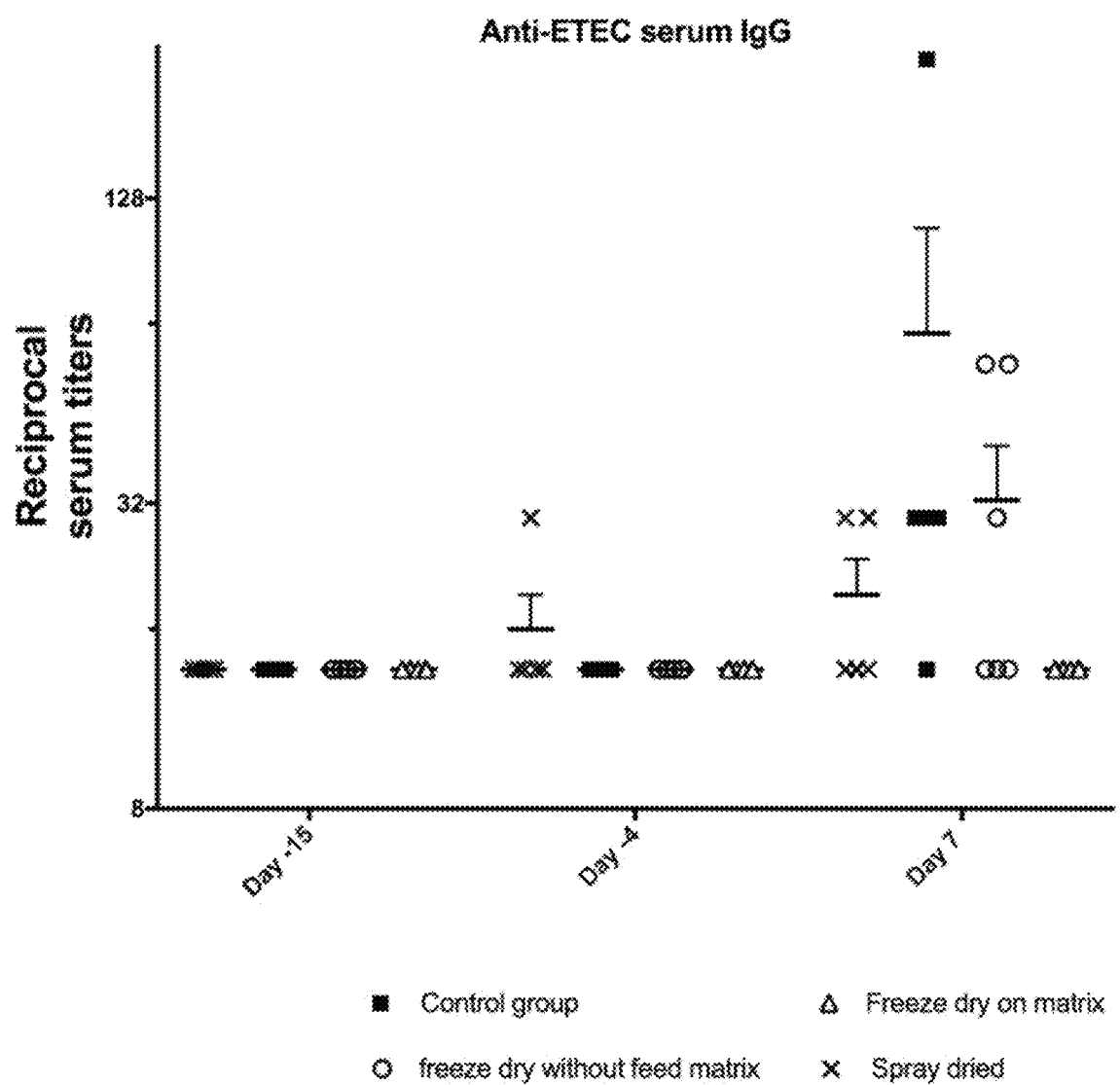
Figure 4D:
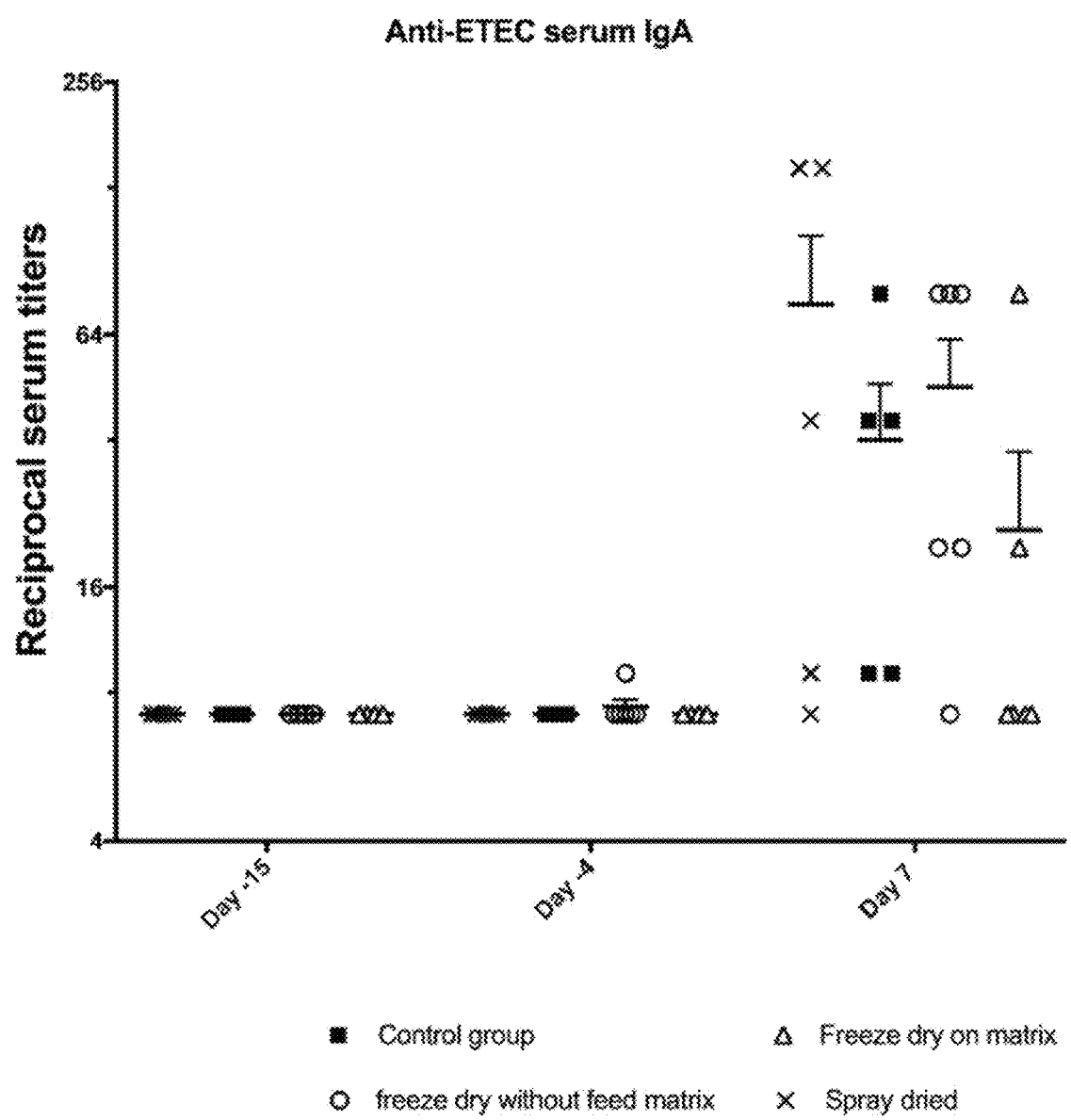

All the piglets of the negative control group shed high CFUs of the F4-ETEC, on day 1 and day 2, and the shedding was maintained at least in half of the piglets till day 3. The overall shedding in the antibody receiving groups was low. FIG. 4B shows the mean shedding in each group and the standard error of the mean (SEM) until day 6, which reflects the efficacious trend of the three *Pichia* produced and differentially processed VHH-IgA-Fc fusions containing diets in preventing the F4-ETEC infection. These data show that the matrix—either as pig feed in freeze drying process, or maltodextrin in spray drying, attributes to a higher efficacy in vivo. The serum anti-ETEC IgG (see FIG. 4C) and IgA (see FIG. 4D) levels were lowest in that group received freeze-dry on feed matrix formulation, which corroborates the shedding results. Overall, variation is individual piglets were observed within the groups showing seroconversion, (error bars in FIGS. 4C and 4D represent standard error of the mean).

Material and Methods for Example 3

*Pichia* Produced VHH-IgA-Fc Based Feed Formulation

The efficacious dose of the anti-ETEC VHH-IgAFc as applied in Example 1, challenge experiment, was about 5 mg VHH-IgAFc or more appropriately, feed formulation bearing dried product from 0.5 L of the shake flask grown culture per piglet per day. This dose was composed of equal parts of the two anti-F4-ETEC VHH-IgAFcs viz. V2A and V3A (see Virdi et al (2013) 110, 29, 11809-11814). To prepare similar dose for 18 piglets, (six animals in each of the three groups) receiving the *Pichia* produced VHH-IgAFcs; 45 L of each V2A and V3A (total 90 L) expressing *Pichia* culture was grown in shake-flasks. This was produced in six batches (in a five day long process, as in Example 1, 48 hrs growth in BMGY medium followed by induction for 48 hrs in BMMY medium) as summarised in Table 5 below. Thus weekly 15 L culture batch was produced. At the end of each run, the culture medium was harvested by centrifugation, the cell free supernatant was concentrated via diafiltration to 1 L and subsequently buffer exchanged with sodium-phosphatebuffer (20 mM $Na_2HPO_4$, 18.75 mM NaCl, pH 6), using Centramate™ 500 S tangential flow filtration system (Pall Life Science) fitted with 5 kDa Omega™ centramate filter cassette. The resultant 1 L retentate protein solution containing *Pichia* produced VHH-IgAFc-termed retentate, obtained at the end of each of the six batches (Table 4), was dried in three specific manners as below.

TABLE 4

The drying process of each batch of *Pichia* produced VHH-IgA-Fc, to formulate the respective experimental feed

| Batch number | Anti-ETEC VHH-IgAFc antibody | Drying process | Feed formulation |
| --- | --- | --- | --- |
| 1 | V2A | 1 L retentate and 1 Kg pig feed slurry freeze-drying | pool of dried powder ~2 Kg + 16 Kg of commercial piglet feed |
| 2 | V3A | 1 L retentate and 1 Kg pig feed slurry freeze-drying | |
| 3 | V2A | 1 L retentate freeze-drying (Without any solid matrix) | pool of dried V2A and V3A powder ~60 g + 17.94 Kg of commercial piglet feed |
| 4 | V3A | 1 L retentate freeze-drying (Without any solid matrix) | |

TABLE 4-continued

The drying process of each batch of *Pichia* produced VHH-IgA-Fc, to formulate the respective experimental feed

| Batch number | Anti-ETEC VHH-IgAFc antibody | Drying process | Feed formulation |
| --- | --- | --- | --- |
| 5 | V3A | 1 L retentate bearing V3A (batch 5) mixed with 1 L retentate bearing V2A (batch 6) together with 10% maltodextrin was spray-drying | Spray dried powder bearing pool of V2A and V3A ~2.3 Kg + 15.7 Kg of feed |
| 6 | V2A | | |

Manner 1: Freeze-dried with matrix (similar to Example 1): one liter of retentate, either bearing VHH-IgAFc V2A (batch 1, Table 5) or V3A (batch 2, Table 4) was mixed with one kilogram of commercial piglet feed (supplier: Van Huffel, 9850 Poesele (Nevele) Belgium) with a hand held paddle to avoid any foaming, and the slurry was lyophilised using freeze dryer (Epsilon 2-10 D LSC-Martin-Christ, Germany) for 47 hours. The resultant dried powder, of the 2 freeze-drying batches (approximately 1 Kg each), containing VHH-IgA-Fc V2A and V3A, respectively, were then mixed with of pig feed to result in 18 Kg of final *Pichia* produced freeze-dried on matrix VHH-IgAFc bearing feed (Table 4).

Manner 2: Freeze-dried without matrix: one liter of retentate, either bearing VHH-IgAFc V2A (batch 3) or V3A (batch 4) was lyophilised using freeze dryer (Epsilon 2-10 D LSC-Martin-Christ, Germany) for 47 hours. The resultant dried powder, of the 2 freeze-drying batches (~30 grams each) containing VHH-IgAFc V2A and V3A, respectively, were then mixed together with of pig feed to result in 18 Kg of final *Pichia* produced freeze-dried-without-matrix VHH-IgAFc bearing feed (Table 4).

Manner 3: Spray-dried: one liter retentate bearing VHH-IgAFc V3A (batch 5, Table 4) and another liter of retentate bearing VHH-IgAFc V2A (batch 6, Table 5), were mixed together with 23 L sodium-phosphate buffer (20 mM $Na_2HPO_4$, 18.75 mM NaCl, pH 6) containing 2.5 Kg of maltodextrin. The total 25 L liquid was mixture thoroughly using industrial blender for 5-7 minutes and then fed into the spray-drier, with parameters set to 45° C. preheating of the feeding liquid, and 170° C. inlet air temperature. During the drying process, the average outlet air temperature was about 80° C., and a constant liquid pumping speed was maintained. Approximately 2.3 kg of dried V2A and V3A bearing powder was recovered, which was mixed together with of pig feed to result in 18 Kg of final *Pichia* produced spray-dried VHH-IgAFc bearing feed (Table 4).

The dried VHH-IgAFcs from each of the differential drying process run (see Table 5), being freeze-dried on feed (V2A batch 1, V3A-batch 2), freeze dried without matrix (V2A-batch 3, V3A batch-4) and spray-dried with maltodextrin (V3A+V2A, batch 5 and batch 6 combined) when solubilized in phosphate buffer saline and evaluated in ELISA were observed to be functionally active as binding to the immobilized F4-FaeG antigen.

The control feed included 18 kg of basic feed without any antibody. Each of the 18 Kg feed formulations were divided into 10 bags of 1.8 Kg each, as daily feed allowance per group, which was provided in the feeding vat for the piglets from day −3 till day 7 (FIG. 4A).

Piglet Challenge Experiment:

The piglet challenge experiments were performed in accordance to the Belgian legislations for animal welfare, upon the approval of Animal Care and Ethics Committee of the Faculty of Veterinary Medicine at Ghent University, Belgium (ethical dossier number EC2017/122). The piglets (breed: hybrid) were bought from farms of the Institute for Agricultural and Fisheries Research (ILVO), Melle, Belgium (ethical dossier no 2017/306). Five primiparous sows were abstained from the booster vaccine against F4-ETEC to ensure low lactogenic immunity. The piglets born to these sows, were administered antibiotic (Duphamox 0.1 ml/piglet) three times, on every other day after birth to protect from the F4-ETEC infection. Further, blood was sampled from these piglets on the 15$^{th}$ day of birth, for evaluating the anti-F4-ETEC serum titres and the MUC13 genotyping assay (Goetstouwers et al (2014) PLoS One 9, e105013), which correlates with the presence of F4-ETEC receptors. Twenty four seronegative and homozygous for the MUC13 F4-ETEC susceptible genotype were selected, weaned and transported to the stables of veterinary faculty of Gent University for the challenge-experiment. The piglets were properly randomized over the feeding groups based on their litter, genotype and weight. The average starting weight of each group was 8.5 Kg. The piglets were administered intramuscular antibiotic-Duphamox (0.6 ml/piglet) on day −12 and day −11; while Baytril (0.25 ml/piglet) was administered on day −8, day −7 and day −6 to prevent the contingency of bacterial infections post transportation. The challenge was performed as previously described (Virdi et al (2013) Proc Nat Acad Sci USA. 110, 29, 11809-11814). Briefly, the piglets were challenged on consecutive days with 10$^{10}$ F4-ETEC bacteria (strain-GIS26R$^{strep}$), via intra-gastric intubation under sedation (1 ml azaperone, Stressnill® Janssen Animal Health), post neutralisation of gastric pH with 60 ml bicarbonate buffer (1.4% NaHCO$_3$ w/v in distilled water). The first day of challenge is accounted as day 0 in the timeline (FIG. 4A). The feed containing antibodies was administered for a period of 10 days, starting three days before the challenge (FIG. 4A). Faecal samples were collected from the day of challenge until day 12 to monitor the shedding of the F4-ETEC challenged strain GIS26R$^{strep}$, on blood agar plates with streptomycin selection (1 mg/ml). Blood samples were taken to monitor the F4-ETEC specific IgG, and IgA titres on day −15 (day of weaning), day −4, day 7. Specific sample collection and manipulations with the animals are schematically represented in FIG. 4A.

The invention claimed is:

1. A dried pharmaceutically acceptable formulation obtained by process comprising:

separating, from a culture medium in which a recombinant fungal host cell has been cultured, macromolecules smaller than 5 kDa so as to obtain a separated culture medium comprising macromolecules larger than 5 kDa; and drying the separated culture medium so as to produce the dried pharmaceutically acceptable formulation, wherein the separating of macromolecules smaller than 5 kDa is the only separation performed on the culture medium to remove macromolecules before drying;

wherein the separated culture medium comprises a polypeptide fused to an Fc domain secreted into the culture medium by the recombinant fungal host cell; and wherein the polypeptide is exogenous to the recombinant fungal host cell.

2. The dried pharmaceutically acceptable formulation of claim 1, wherein the polypeptide is a prophylactic or therapeutic peptide or wherein the polypeptide is a vaccine or forms part of a vaccine.

3. The dried pharmaceutically acceptable formulation of claim 1, wherein an oral admissible matrix is added to the separated medium prior to drying.

4. The dried pharmaceutically acceptable formulation of claim 1, wherein the Fc domain is an IgA Fc domain.

5. The dried pharmaceutically acceptable formulation of claim 1, wherein the drying is carried out by spray-drying or by lyophilisation.

6. The dried pharmaceutically acceptable formulation of claim 1, wherein the dried formulation is a medicament.

7. The dried pharmaceutically acceptable formulation of claim 1, wherein the dried formulation comprises a pharmaceutical excipient.

8. The dried pharmaceutically acceptable formulation of claim 6, wherein the medicament is a medicament for the treatment of gastro-intestinal diseases.

9. The dried pharmaceutically acceptable formulation of claim 6, wherein the medicament is a medicament for the treatment of buccal diseases.

10. The dried pharmaceutically acceptable formulation of claim 1, wherein the dried formulation is a vaccine.

11. The dried pharmaceutically acceptable formulation of claim 1, wherein the dried formulation forms part of a feed product or food product.

12. The dried pharmaceutically acceptable formulation of claim 11, wherein the food product is a functional or medicinal food product.

13. The dried pharmaceutically acceptable formulation of claim 1, wherein the polypeptide is IL22.

14. The dried pharmaceutically acceptable formulation of claim 1, wherein the polypeptide is an immunoglobulin single variable domain.

15. A method of making the dried pharmaceutically acceptable formulation of claim 1, the method comprising:

separating, from a culture medium in which a recombinant fungal host cell has been cultured, macromolecules smaller than 5 kDa so as to obtain a separated culture medium having a lowered concentration of macromolecules smaller than 5 kDa as compared to the culture medium immediately prior to the separation; and drying the separated culture medium so as to produce the dried formulation of claim 1, wherein the separated culture medium comprises a polypeptide fused to an Fc domain secreted into the culture medium by the recombinant fungal host cell; and wherein the polypeptide is exogenous to the recombinant fungal host cell.

16. The dried pharmaceutical formulation of claim 3, wherein the dried pharmaceutically acceptable formulation is a vaccine.

17. The dried pharmaceutical formulation of claim 1, wherein the recombinant fungal host cell has been removed from the culture medium prior to subjecting the culture medium to separation.

* * * * *